(12) United States Patent
Miller

(10) Patent No.: US 9,393,031 B2
(45) Date of Patent: Jul. 19, 2016

(54) APPARATUS AND METHOD TO PROVIDE EMERGENCY ACCESS TO BONE MARROW

(71) Applicant: VIDACARE LLC, Shavano Park, TX (US)

(72) Inventor: Larry J. Miller, Spring Branch, TX (US)

(73) Assignee: Vidacare LLC, Wayne, PA (US)

( * ) Notice: Subject to any disclaimer, the term of this patent is extended or adjusted under 35 U.S.C. 154(b) by 0 days.

(21) Appl. No.: 14/666,391

(22) Filed: Mar. 24, 2015

(65) Prior Publication Data

US 2015/0366569 A1 Dec. 24, 2015

Related U.S. Application Data

(62) Division of application No. 14/271,144, filed on May 6, 2014, now Pat. No. 8,992,535, which is a division of application No. 12/331,979, filed on Dec. 10, 2008, now Pat. No. 8,715,287, which is a division of application No. 10/449,503, filed on May 30, 2003, now Pat. No. 7,670,328.

(60) Provisional application No. 60/384,756, filed on May 31, 2002.

(51) Int. Cl.
*A61B 17/00* (2006.01)
*A61F 2/46* (2006.01)
(Continued)

(52) U.S. Cl.
CPC .......... *A61B 17/1671* (2013.01); *A61B 10/025* (2013.01); *A61B 10/0283* (2013.01); *A61B 17/1613* (2013.01); *A61B 17/32002* (2013.01); *A61B 17/32053* (2013.01); *A61B 17/3472* (2013.01); *A61B 17/3476* (2013.01); *A61M 5/158* (2013.01); *A61B 17/1637* (2013.01); *A61B 19/0271* (2013.01); *A61B 19/201* (2013.01); *A61B 19/34* (2013.01);
(Continued)

(58) Field of Classification Search
USPC .............. 606/167, 80, 86 R, 329, 104, 62, 95
See application file for complete search history.

(56) References Cited

U.S. PATENT DOCUMENTS

| 1,539,637 A | 5/1925 | Bronner et al. |
| 2,317,648 A | 4/1943 | Siqveland et al. |

(Continued)

FOREIGN PATENT DOCUMENTS

| CA | 2138842 A1 | 6/1996 |
| CA | 2454600 A1 | 2/2003 |

(Continued)

OTHER PUBLICATIONS

"Proven reliability for quality bone marrow samples", Special Procedures, Cardinal Health, 6 pages (2003).

(Continued)

*Primary Examiner* — Sameh Boles
(74) *Attorney, Agent, or Firm* — Baker & Hostetler LLP

(57) ABSTRACT

An apparatus and method for penetrating the bone marrow is provided. The apparatus includes a housing, a penetrator assembly, operable to penetrate the bone marrow, a connector operable to releasably attach the penetrator assembly to a drill shaft, the drill shaft operable to connect the penetrator assembly to a gear assembly, a gear assembly operable to engage and rotate the drill shaft, a motor operable to engage the reduction gear assembly and drive the penetrator into the bone marrow by rotation of the drill shaft, and a power supply and associated circuitry operable to power the motor. The apparatus and method may be adapted to insert a probe through the skull and into the brain.

14 Claims, 28 Drawing Sheets

(51) Int. Cl.

| | | |
|---|---|---|
| *A61B 17/16* | (2006.01) | |
| *A61B 10/02* | (2006.01) | |
| *A61B 17/32* | (2006.01) | |
| *A61B 17/3205* | (2006.01) | |
| *A61B 17/34* | (2006.01) | |
| *A61M 5/158* | (2006.01) | |
| *A61B 19/02* | (2006.01) | |
| *A61B 19/00* | (2006.01) | |
| *A61M 1/00* | (2006.01) | |

(52) U.S. Cl.
CPC ...... *A61B 2010/0208* (2013.01); *A61B 2010/0258* (2013.01); *A61B 2017/0046* (2013.01); *A61B 2017/00398* (2013.01); *A61B 2017/00734* (2013.01); *A61B 2017/320024* (2013.01); *A61B 2017/3405* (2013.01); *A61B 2019/0278* (2013.01); *A61B 2019/304* (2013.01); *A61B 2019/4868* (2013.01); *A61B 2217/005* (2013.01); *A61M 1/008* (2013.01); *A61M 2005/1581* (2013.01); *A61M 2005/1585* (2013.01); *A61M 2210/02* (2013.01)

(56) References Cited

U.S. PATENT DOCUMENTS

| | | |
|---|---|---|
| 2,419,045 A | 4/1947 | Whittaker et al. |
| 2,773,501 A | 12/1956 | Young et al. |
| 3,104,448 A | 9/1963 | Morrow et al. |
| 3,120,845 A | 2/1964 | Horner et al. |
| 3,173,417 A | 3/1965 | Horner et al. |
| 3,175,554 A | 3/1965 | Stewart et al. |
| 3,507,276 A | 4/1970 | Burgess et al. |
| 3,529,580 A | 9/1970 | Stevens et al. |
| 3,543,966 A | 12/1970 | Ryan et al. |
| 3,750,667 A | 8/1973 | Pshenichny et al. |
| 3,815,605 A | 6/1974 | Schmidt et al. |
| 3,835,860 A | 9/1974 | Garretson |
| 3,893,445 A | 7/1975 | Hofsess |
| 3,991,765 A | 11/1976 | Cohen |
| 4,021,920 A | 5/1977 | Kirschner et al. |
| 4,099,518 A | 7/1978 | Baylis et al. |
| 4,124,026 A | 11/1978 | Berner et al. |
| 4,142,517 A | 3/1979 | Contreras Guerrero de Stavropoulos et al. |
| 4,170,993 A | 10/1979 | Alvarez |
| 4,185,619 A | 1/1980 | Reiss |
| 4,194,505 A | 3/1980 | Schmitz |
| 4,258,722 A | 3/1981 | Sessions et al. |
| 4,262,676 A | 4/1981 | Jamshidi |
| 4,306,570 A | 12/1981 | Matthews |
| 4,333,459 A | 6/1982 | Becker |
| 4,381,777 A | 5/1983 | Garnier |
| 4,399,723 A | 8/1983 | Marleau |
| 4,441,563 A | 4/1984 | Walton, II |
| 4,469,109 A | 9/1984 | Mehl |
| 4,484,577 A | 11/1984 | Sackner et al. |
| 4,543,966 A | 10/1985 | Islam et al. |
| 4,553,539 A | 11/1985 | Morris |
| 4,578,064 A | 3/1986 | Sarnoff et al. |
| 4,605,011 A | 8/1986 | Naslund |
| 4,620,539 A | 11/1986 | Andrews et al. |
| 4,646,731 A | 3/1987 | Brower |
| 4,654,492 A | 3/1987 | Koerner et al. |
| 4,655,226 A | 4/1987 | Lee |
| 4,659,329 A | 4/1987 | Annis |
| 4,692,073 A | 9/1987 | Martindell |
| 4,711,636 A | 12/1987 | Bierman |
| 4,713,061 A | 12/1987 | Tarello et al. |
| 4,716,901 A | 1/1988 | Jackson et al. |
| 4,723,945 A | 2/1988 | Theiling |
| 4,758,225 A | 7/1988 | Cox et al. |
| 4,762,118 A | 8/1988 | Lia et al. |
| 4,772,261 A | 9/1988 | Von Hoff et al. |
| 4,787,893 A | 11/1988 | Villette |
| 4,793,363 A | 12/1988 | Ausherman et al. |
| 4,867,158 A | 9/1989 | Sugg |
| 4,919,146 A | 4/1990 | Rhinehart et al. |
| 4,921,013 A | 5/1990 | Spalink et al. |
| 4,935,010 A | 6/1990 | Cox et al. |
| 4,940,459 A | 7/1990 | Noce |
| 4,944,677 A | 7/1990 | Alexandre |
| 4,969,870 A | 11/1990 | Kramer et al. |
| 4,986,279 A | 1/1991 | O'Neill |
| 5,002,546 A | 3/1991 | Romano |
| 5,025,797 A | 6/1991 | Baran |
| 5,036,860 A | 8/1991 | Leigh et al. |
| 5,057,085 A | 10/1991 | Kopans |
| 5,074,311 A | 12/1991 | Hasson |
| 5,116,324 A | 5/1992 | Brierley et al. |
| 5,120,312 A | 6/1992 | Wigness et al. |
| 5,122,114 A | 6/1992 | Miller et al. |
| 5,133,359 A | 7/1992 | Kedem |
| 5,137,518 A | 8/1992 | Mersch |
| 5,139,500 A | 8/1992 | Schwartz |
| 5,145,369 A | 9/1992 | Lustig et al. |
| 5,172,701 A | 12/1992 | Leigh |
| 5,172,702 A | 12/1992 | Leigh et al. |
| 5,176,643 A | 1/1993 | Kramer et al. |
| 5,195,985 A | 3/1993 | Hall |
| 5,203,056 A | 4/1993 | Funk et al. |
| 5,207,697 A | 5/1993 | Carusillo et al. |
| 5,249,583 A | 10/1993 | Mallaby |
| 5,257,632 A | 11/1993 | Turkel et al. |
| 5,261,877 A | 11/1993 | Fine et al. |
| 5,269,785 A | 12/1993 | Bonutti |
| 5,271,414 A | 12/1993 | Partika et al. |
| 5,279,306 A | 1/1994 | Mehl |
| 5,312,364 A | 5/1994 | Jacobs |
| 5,312,408 A | 5/1994 | Brown |
| 5,315,737 A | 5/1994 | Ouimet |
| 5,324,300 A | 6/1994 | Elias et al. |
| 5,332,398 A | 7/1994 | Miller et al. |
| 5,333,790 A | 8/1994 | Christopher |
| 5,341,823 A | 8/1994 | Manosalva et al. |
| 5,348,022 A | 9/1994 | Leigh et al. |
| 5,357,974 A | 10/1994 | Baldridge |
| 5,368,046 A | 11/1994 | Scarfone et al. |
| 5,372,583 A | 12/1994 | Roberts et al. |
| 5,383,859 A | 1/1995 | Sewell, Jr. |
| 5,385,553 A | 1/1995 | Hart et al. |
| 5,389,553 A | 2/1995 | Grubisich et al. |
| 5,400,798 A | 3/1995 | Baran |
| 5,405,348 A | 4/1995 | Anspach et al. |
| 5,405,362 A | 4/1995 | Kramer et al. |
| 5,423,824 A | 6/1995 | Akerfeldt et al. |
| 5,431,655 A | 7/1995 | Melker et al. |
| 5,451,210 A | 9/1995 | Kramer et al. |
| 5,484,442 A | 1/1996 | Melker et al. |
| D369,858 S | 5/1996 | Baker et al. |
| 5,526,821 A | 6/1996 | Jamshidi |
| 5,529,580 A | 6/1996 | Kusunoki et al. |
| 5,549,565 A | 8/1996 | Ryan et al. |
| 5,554,154 A | 9/1996 | Rosenberg |
| 5,556,399 A | 9/1996 | Huebner |
| 5,558,737 A | 9/1996 | Brown et al. |
| 5,571,133 A | 11/1996 | Yoon |
| 5,586,847 A | 12/1996 | Mattern, Jr. et al. |
| 5,591,188 A | 1/1997 | Waisman |
| 5,595,186 A | 1/1997 | Rubinstein et al. |
| 5,601,559 A | 2/1997 | Melker et al. |
| 5,632,747 A | 5/1997 | Scarborough et al. |
| 5,672,155 A | 9/1997 | Riley et al. |
| 5,713,368 A | 2/1998 | Leigh |
| 5,724,873 A | 3/1998 | Hillinger |
| 5,733,262 A | 3/1998 | Paul |
| 5,752,923 A | 5/1998 | Terwilliger |
| 5,762,639 A | 6/1998 | Gibbs |
| 5,766,221 A | 6/1998 | Benderev et al. |
| 5,769,086 A | 6/1998 | Ritchart et al. |
| 5,779,708 A | 7/1998 | Wu |
| 5,800,389 A | 9/1998 | Burney et al. |
| 5,807,277 A | 9/1998 | Swaim |

(56) References Cited

U.S. PATENT DOCUMENTS

| | | |
|---|---|---|
| 5,810,826 A | 9/1998 | Akerfeldt et al. |
| 5,817,052 A | 10/1998 | Johnson et al. |
| 5,823,970 A | 10/1998 | Terwilliger |
| D403,405 S | 12/1998 | Terwilliger |
| 5,858,005 A | 1/1999 | Kriesel |
| 5,865,711 A | 2/1999 | Chen |
| 5,868,711 A | 2/1999 | Kramer et al. |
| 5,868,750 A | 2/1999 | Schultz |
| 5,873,510 A | 2/1999 | Hirai et al. |
| 5,885,226 A | 3/1999 | Rubinstein et al. |
| 5,891,085 A | 4/1999 | Lilley et al. |
| 5,911,701 A | 6/1999 | Miller et al. |
| 5,911,708 A | 6/1999 | Teirstein |
| 5,916,229 A | 6/1999 | Evans |
| 5,919,172 A | 7/1999 | Golba, Jr. |
| 5,924,864 A | 7/1999 | Loge et al. |
| 5,927,976 A | 7/1999 | Wu |
| 5,928,238 A | 7/1999 | Scarborough et al. |
| 5,941,706 A | 8/1999 | Ura |
| 5,941,851 A | 8/1999 | Coffey et al. |
| 5,960,797 A | 10/1999 | Kramer et al. |
| 5,980,545 A | 11/1999 | Pacala et al. |
| 5,993,417 A | 11/1999 | Yerfino et al. |
| 5,993,454 A | 11/1999 | Longo |
| 6,007,496 A | 12/1999 | Brannon |
| 6,017,348 A | 1/2000 | Hart et al. |
| 6,018,094 A | 1/2000 | Fox |
| 6,018,230 A | 1/2000 | Casey |
| 6,022,324 A | 2/2000 | Skinner |
| 6,027,458 A | 2/2000 | Janssens |
| 6,033,369 A | 3/2000 | Goldenberg |
| 6,033,411 A | 3/2000 | Preissman |
| 6,042,585 A | 3/2000 | Norman |
| 6,049,725 A | 4/2000 | Emmert et al. |
| 6,063,037 A | 5/2000 | Mettermeier et al. |
| 6,066,938 A | 5/2000 | Hyodo et al. |
| 6,071,284 A | 6/2000 | Fox |
| 6,080,115 A | 6/2000 | Rubinstein |
| 6,083,176 A | 7/2000 | Terwilliger |
| 6,086,543 A | 7/2000 | Anderson et al. |
| 6,086,544 A | 7/2000 | Hibner et al. |
| 6,096,042 A | 8/2000 | Herbert |
| 6,102,915 A | 8/2000 | Bresler et al. |
| 6,106,484 A | 8/2000 | Terwilliger |
| 6,110,128 A | 8/2000 | Andelin et al. |
| 6,110,129 A | 8/2000 | Terwilliger |
| 6,110,174 A | 8/2000 | Nichter |
| 6,120,462 A | 9/2000 | Hibner et al. |
| 6,135,769 A | 10/2000 | Kwan |
| 6,159,163 A | 12/2000 | Strauss et al. |
| 6,162,203 A | 12/2000 | Haaga |
| 6,183,442 B1 | 2/2001 | Athanasiou |
| 6,210,376 B1 | 4/2001 | Grayson |
| 6,217,561 B1 | 4/2001 | Gibbs |
| 6,221,029 B1 | 4/2001 | Mathis et al. |
| 6,228,049 B1 | 5/2001 | Schroeder et al. |
| 6,228,088 B1 | 5/2001 | Miller et al. |
| 6,238,355 B1 | 5/2001 | Daum |
| 6,247,928 B1 | 6/2001 | Meller et al. |
| 6,248,110 B1 | 6/2001 | Reiley et al. |
| 6,257,351 B1 | 7/2001 | Ark et al. |
| 6,267,763 B1 | 7/2001 | Castro |
| 6,273,715 B1 | 8/2001 | Meller et al. |
| 6,273,862 B1 | 8/2001 | Privitera et al. |
| 6,283,925 B1 | 9/2001 | Terwilliger |
| 6,283,970 B1 | 9/2001 | Lubinus |
| 6,287,114 B1 | 9/2001 | Meller et al. |
| 6,302,852 B1 | 10/2001 | Fleming, III et al. |
| 6,309,358 B1 | 10/2001 | Okubo |
| 6,312,394 B1 | 11/2001 | Fleming, III |
| 6,315,737 B1 | 11/2001 | Skinner |
| 6,325,806 B1 | 12/2001 | Fox |
| 6,328,701 B1 | 12/2001 | Terwilliger |
| 6,328,744 B1 | 12/2001 | Harari et al. |
| 6,358,252 B1 | 3/2002 | Shapira |
| 6,402,701 B1 | 6/2002 | Kaplan et al. |
| 6,419,490 B1 | 7/2002 | Kitchings Weathers, Jr. |
| 6,425,888 B1 | 7/2002 | Embleton et al. |
| 6,428,487 B1 | 8/2002 | Burdorff et al. |
| 6,443,910 B1 | 9/2002 | Krueger et al. |
| 6,458,117 B1 | 10/2002 | Pollins, Sr. |
| 6,468,248 B1 | 10/2002 | Gibbs |
| 6,478,751 B1 | 11/2002 | Krueger et al. |
| 6,488,636 B2 | 12/2002 | Bryan et al. |
| 6,523,698 B1 | 2/2003 | Dennehey et al. |
| 6,527,736 B1 | 3/2003 | Attinger et al. |
| 6,527,778 B2 | 3/2003 | Athanasiou et al. |
| 6,540,694 B1 | 4/2003 | Van Bladel et al. |
| 6,547,511 B1 | 4/2003 | Adams |
| 6,547,561 B2 | 4/2003 | Meller et al. |
| 6,550,786 B2 | 4/2003 | Gifford et al. |
| 6,554,779 B2 | 4/2003 | Viola et al. |
| 6,555,212 B2 | 4/2003 | Boiocchi et al. |
| 6,575,919 B1 | 6/2003 | Reiley et al. |
| 6,582,399 B1 | 6/2003 | Smith et al. |
| 6,585,622 B1 | 7/2003 | Shum et al. |
| 6,595,911 B2 | 7/2003 | LoVuolo |
| 6,595,979 B1 | 7/2003 | Epstein et al. |
| 6,613,054 B2 | 9/2003 | Scribner et al. |
| 6,616,632 B2 | 9/2003 | Sharp et al. |
| 6,620,111 B2 | 9/2003 | Stephens et al. |
| 6,626,848 B2 | 9/2003 | Neuenfeldt |
| 6,626,887 B1 | 9/2003 | Wu |
| 6,638,235 B2 | 10/2003 | Miller et al. |
| 6,656,133 B2 | 12/2003 | Voegele et al. |
| 6,689,072 B2 | 2/2004 | Kaplan et al. |
| 6,702,760 B2 | 3/2004 | Krause et al. |
| 6,702,761 B1 | 3/2004 | Damadian et al. |
| 6,706,016 B2 | 3/2004 | Cory et al. |
| 6,716,192 B1 | 4/2004 | Orosz, Jr. |
| 6,716,215 B1 | 4/2004 | David et al. |
| 6,716,216 B1 | 4/2004 | Boucher et al. |
| 6,730,043 B2 | 5/2004 | Krueger et al. |
| 6,730,044 B2 | 5/2004 | Stephens et al. |
| 6,749,576 B2 | 6/2004 | Bauer |
| 6,752,768 B2 | 6/2004 | Burdorff et al. |
| 6,752,816 B2 | 6/2004 | Culp et al. |
| 6,758,824 B1 | 7/2004 | Miller et al. |
| 6,761,726 B1 | 7/2004 | Findlay et al. |
| 6,796,957 B2 | 9/2004 | Carpenter et al. |
| 6,846,314 B2 | 1/2005 | Shapira |
| 6,849,051 B2 | 2/2005 | Sramek et al. |
| 6,855,148 B2 | 2/2005 | Foley et al. |
| 6,860,860 B2 | 3/2005 | Viola |
| 6,875,183 B2 | 4/2005 | Cervi |
| 6,875,219 B2 | 4/2005 | Arramon et al. |
| 6,884,245 B2 | 4/2005 | Spranza, III |
| 6,887,209 B2 | 5/2005 | Kadziauskas et al. |
| 6,890,308 B2 | 5/2005 | Islam |
| 6,905,486 B2 | 6/2005 | Gibbs |
| 6,930,461 B2 | 8/2005 | Rutkowski |
| 6,942,669 B2 | 9/2005 | Kurc |
| 6,969,373 B2 | 11/2005 | Schwartz et al. |
| 7,008,381 B2 | 3/2006 | Janssens |
| 7,008,383 B1 | 3/2006 | Damadian et al. |
| 7,008,394 B2 | 3/2006 | Geise et al. |
| 7,025,732 B2 | 4/2006 | Thompson et al. |
| 7,063,672 B2 | 6/2006 | Schramm |
| 7,137,985 B2 | 11/2006 | Jahng |
| 7,186,257 B2 | 3/2007 | Kim |
| 7,207,949 B2 | 4/2007 | Miles et al. |
| 7,226,450 B2 | 6/2007 | Athanasiou et al. |
| 7,229,401 B2 | 6/2007 | Kindlein |
| 7,670,328 B2 | 3/2010 | Miller |
| 7,699,850 B2 | 4/2010 | Miller |
| 7,811,260 B2 | 10/2010 | Miller et al. |
| 7,815,642 B2 | 10/2010 | Miller |
| 7,850,620 B2 | 12/2010 | Miller et al. |
| 7,951,089 B2 | 5/2011 | Miller |
| 8,038,664 B2 | 10/2011 | Miller et al. |
| 8,217,561 B2 | 7/2012 | Fukuzawa et al. |
| 8,419,683 B2 | 4/2013 | Miller et al. |
| 8,480,632 B2 | 7/2013 | Miller et al. |
| 8,506,568 B2 | 8/2013 | Miller |

(56) References Cited

U.S. PATENT DOCUMENTS

| | | |
|---|---|---|
| 8,668,698 B2 | 3/2014 | Miller et al. |
| 8,684,978 B2 | 4/2014 | Miller et al. |
| 8,690,791 B2 | 4/2014 | Miller |
| 8,715,287 B2 | 5/2014 | Miller |
| 2001/0005778 A1 | 6/2001 | Ouchi |
| 2001/0014439 A1 | 8/2001 | Meller et al. |
| 2001/0047183 A1 | 11/2001 | Privitera et al. |
| 2001/0053888 A1 | 12/2001 | Athanasiou et al. |
| 2002/0042581 A1 | 4/2002 | Cervi |
| 2002/0055713 A1 | 5/2002 | Gibbs |
| 2002/0120212 A1 | 8/2002 | Ritchart et al. |
| 2002/0138021 A1 | 9/2002 | Pflueger |
| 2002/0151902 A1 | 10/2002 | Riedel et al. |
| 2003/0028146 A1 | 2/2003 | Aves |
| 2003/0032939 A1 | 2/2003 | Gibbs |
| 2003/0036747 A1 | 2/2003 | Le et al. |
| 2003/0050574 A1 | 3/2003 | Krueger |
| 2003/0114858 A1 | 6/2003 | Athanasiou et al. |
| 2003/0125639 A1 | 7/2003 | Fisher et al. |
| 2003/0153842 A1 | 8/2003 | Lamoureux et al. |
| 2003/0191414 A1 | 10/2003 | Reiley et al. |
| 2003/0195436 A1 | 10/2003 | Van Bladel et al. |
| 2003/0195524 A1 | 10/2003 | Barner |
| 2003/0199787 A1 | 10/2003 | Schwindt |
| 2003/0216667 A1 | 11/2003 | Viola |
| 2003/0225344 A1 | 12/2003 | Miller |
| 2003/0225364 A1 | 12/2003 | Kraft et al. |
| 2003/0225411 A1 | 12/2003 | Miller |
| 2004/0019297 A1 | 1/2004 | Angel |
| 2004/0019299 A1 | 1/2004 | Ritchart et al. |
| 2004/0034280 A1 | 2/2004 | Privitera et al. |
| 2004/0049128 A1 | 3/2004 | Miller et al. |
| 2004/0064136 A1 | 4/2004 | Papineau et al. |
| 2004/0073139 A1 | 4/2004 | Hirsch et al. |
| 2004/0092946 A1 | 5/2004 | Bagga et al. |
| 2004/0153003 A1 | 8/2004 | Cicenas et al. |
| 2004/0158172 A1 | 8/2004 | Hancock |
| 2004/0158173 A1 | 8/2004 | Voegele et al. |
| 2004/0162505 A1 | 8/2004 | Kaplan et al. |
| 2004/0191897 A1 | 9/2004 | Muschler |
| 2004/0210161 A1 | 10/2004 | Burdorff et al. |
| 2004/0215102 A1 | 10/2004 | Ikehara et al. |
| 2004/0220497 A1 | 11/2004 | Findlay et al. |
| 2005/0027210 A1 | 2/2005 | Miller |
| 2005/0040060 A1 | 2/2005 | Andersen et al. |
| 2005/0075581 A1 | 4/2005 | Schwindt |
| 2005/0085838 A1 | 4/2005 | Thompson et al. |
| 2005/0101880 A1 | 5/2005 | Cicenas et al. |
| 2005/0113716 A1 | 5/2005 | Mueller et al. |
| 2005/0119660 A1 | 6/2005 | Bourlion et al. |
| 2005/0124915 A1 | 6/2005 | Eggers et al. |
| 2005/0131345 A1 | 6/2005 | Miller |
| 2005/0148940 A1 | 7/2005 | Miller |
| 2005/0165328 A1 | 7/2005 | Heske et al. |
| 2005/0165403 A1 | 7/2005 | Miller |
| 2005/0165404 A1 | 7/2005 | Miller |
| 2005/0171504 A1 | 8/2005 | Miller |
| 2005/0182394 A1 | 8/2005 | Spero et al. |
| 2005/0200087 A1 | 9/2005 | Vasudeva et al. |
| 2005/0203439 A1 | 9/2005 | Heske et al. |
| 2005/0209530 A1 | 9/2005 | Pflueger |
| 2005/0215921 A1 | 9/2005 | Hibner et al. |
| 2005/0228309 A1 | 10/2005 | Fisher et al. |
| 2005/0261693 A1 | 11/2005 | Miller et al. |
| 2006/0011506 A1 | 1/2006 | Riley |
| 2006/0015066 A1 | 1/2006 | Turieo et al. |
| 2006/0036212 A1 | 2/2006 | Miller |
| 2006/0052790 A1 | 3/2006 | Miller |
| 2006/0074345 A1 | 4/2006 | Hibner |
| 2006/0079774 A1 | 4/2006 | Anderson |
| 2006/0089565 A1 | 4/2006 | Schramm |
| 2006/0115066 A1 | 6/2006 | Levien et al. |
| 2006/0122535 A1 | 6/2006 | Daum |
| 2006/0129082 A1 | 6/2006 | Rozga |
| 2006/0144548 A1 | 7/2006 | Beckman et al. |
| 2006/0149163 A1 | 7/2006 | Hibner et al. |
| 2006/0167377 A1 | 7/2006 | Ritchart et al. |
| 2006/0167378 A1 | 7/2006 | Miller |
| 2006/0167379 A1 | 7/2006 | Miller |
| 2006/0184063 A1 | 8/2006 | Miller |
| 2006/0189940 A1 | 8/2006 | Kirsch |
| 2006/0206132 A1 | 9/2006 | Conquergood et al. |
| 2007/0016100 A1 | 1/2007 | Miller |
| 2007/0049945 A1 | 3/2007 | Miller |
| 2007/0149920 A1 | 6/2007 | Michels et al. |
| 2007/0213735 A1 | 9/2007 | Saadat et al. |
| 2007/0270775 A1 | 11/2007 | Miller et al. |
| 2008/0015467 A1 | 1/2008 | Miller |
| 2008/0015468 A1 | 1/2008 | Miller |
| 2008/0045857 A1 | 2/2008 | Miller et al. |
| 2008/0045860 A1 | 2/2008 | Miller et al. |
| 2008/0045861 A1 | 2/2008 | Miller et al. |
| 2008/0045965 A1 | 2/2008 | Miller et al. |
| 2008/0140014 A1 | 6/2008 | Miller et al. |
| 2008/0215056 A1 | 9/2008 | Miller et al. |
| 2008/0221580 A1 | 9/2008 | Miller et al. |
| 2009/0069716 A1 | 3/2009 | Freeman et al. |
| 2009/0093677 A1 | 4/2009 | Smith |
| 2009/0194446 A1 | 8/2009 | Miller et al. |
| 2010/0204611 A1 | 8/2010 | Zambelli |
| 2011/0046507 A1 | 2/2011 | Herndon |
| 2011/0082387 A1 | 4/2011 | Miller et al. |
| 2011/0306841 A1 | 12/2011 | Lozman et al. |
| 2012/0165832 A1 | 6/2012 | Oostman, Jr. et al. |

FOREIGN PATENT DOCUMENTS

| | | |
|---|---|---|
| CN | 2320209 Y | 5/1999 |
| CN | 2664675 Y | 12/2004 |
| DE | 10057931 A1 | 8/2002 |
| EP | 0517000 A2 | 12/1992 |
| EP | 0807412 A1 | 11/1997 |
| EP | 1314452 A1 | 5/2003 |
| EP | 1421907 A1 | 5/2004 |
| EP | 1447050 A2 | 8/2004 |
| FR | 2457105 A1 | 12/1980 |
| FR | 2516386 A1 | 5/1983 |
| GB | 2130890 A | 6/1984 |
| JP | H06-132663 A | 5/1994 |
| JP | H10-52433 A | 2/1998 |
| JP | 2001-505076 A | 4/2001 |
| WO | 9208410 A1 | 5/1992 |
| WO | 9307819 A2 | 4/1993 |
| WO | 9631164 A1 | 10/1996 |
| WO | 9806337 A1 | 2/1998 |
| WO | 9852638 A2 | 11/1998 |
| WO | 9918866 A1 | 4/1999 |
| WO | 9952444 A1 | 10/1999 |
| WO | 0009024 A1 | 2/2000 |
| WO | 0056220 A1 | 9/2000 |
| WO | 0178590 A1 | 10/2001 |
| WO | 0241792 A1 | 5/2002 |
| WO | 02096497 A1 | 12/2002 |
| WO | 03015637 A1 | 2/2003 |
| WO | 2005072625 A2 | 8/2005 |
| WO | 2005110259 A1 | 11/2005 |
| WO | 2005112800 A2 | 12/2005 |
| WO | 2008033874 A2 | 3/2008 |
| WO | 2008081438 A1 | 7/2008 |
| WO | 2011123703 A1 | 10/2011 |

OTHER PUBLICATIONS

Astrom, K. Gunnar, "CT-guided Transsternal Core Biopsy of Anterior Mediastinal Masses," Radiology 1996; 199:564-567 (May 1996).

Astrom, K. Gunnar, "Automatic Biopsy instruments Used Through a Coaxial Bone Biopsy System with an Eccentric Drill Tip," Acta Radiological, 1995; 36:237-242 (May 1995).

Australian Exam Report on Patent Application No. 2003240970, 2 pages (Oct. 15, 2007).

BioAccess.com, Single Use Small Bone Power Tool—How it Works, 1 page (Jun. 9, 2008).

(56) References Cited

OTHER PUBLICATIONS

Buckley et al., CT-guided bone biopsy: Initial experience with commercially available hand held Black and Decker drill, European Journal of Radiology 61, pp. 176-180 (2007).
Chinese Office Action; Application No. 200680021872.X; 8 pages (Nov. 6, 2009).
Chinese Office Action; Application No. 200780000585.5; 15 pages (Nov. 9, 2010).
Chinese Office Action; Application No. 200910006631.3; 12 pages (Mar. 11, 2010).
Chinese Office Action, Application No. 2005800003261, 9 pages (Jan. 16, 2009).
Chinese Office Action, Application No. 200780000590.6, 13 pages (Aug. 21, 2009).
Communication Pursuant to Article 94(3) EPC, Application No. 05 712 091.7-1265, 4 pages (Apr. 8, 2008).
Communication relating to the results of the partial International Search Report for PCT/US2005/002484, 6 pages (May 19, 2005).
Cummins, Richard, et al, "ACLS-Principles and Practice", ACLS-The Reference Textbook, American Heart Association, pp. 214-218 (2003).
European Extended Search Report, Application No. EP08021732.6, 7 pages (Nov. 13, 2009).
European Extended Search Report, Application No. EP10153350.3, 5 pages (Mar. 11, 2010).
European Office Action and Search Report, Application No. 09150973.7, 8 pages (Oct. 23, 2009).
European Office Action Communication, Application No. 08158699.2-1265/1967142, 10 pages (Nov. 4, 2008).
European Office Action, Application No. EP03731475.4, 4 pages (Oct. 11, 2007).
European Office Action; Application No. 09 155 111.9-2310; 3 pages (Nov. 25, 2009).
European Search Report, Application No. 08158699.2-1265, 4 pages (Aug. 2008).
F.A.S.T. 1 Intraosseous Infusion System with Depth-Control Mechanism Brochure, 6 pages (2000).
Gunal et al., Compartment Syndrome After Intraosseous Infusion: An Experimental Study in Docs, Journal of Pediatric Survey, vol. 31, No. 11, pp. 1491-1493 (Nov. 1996).
Hakan et al., CT-guided Bone Biopsy Performed by Means of Coaxial Biopsy System with an Eccentric Drill, Radiology, pp. 549-552 (Aug. 1993).
International PCT Search Report and Written Opinion, PCT/US2005/002484, 15 pages (Jul. 22, 2005).
International PCT Search Report and Written Opinion, PCT/US2004/037753, 16 pages (Jul. 8, 2005).
International PCT Search Report, PCT/US03/17167, 8 pages (Sep. 16, 2003).
International PCT Search Report, PCT/US03/17203, 8 pages (Sep. 16, 2003).
International PCT Search Report, PCT/US2004/037753, 6 pages (Apr. 19, 2005).
International Preliminary Report on Patentability, PCT/US2005/002484, 9 pages (Aug. 3, 2006).
International Preliminary Report on Patentability, PCT/US2007/072202, 10 pages (Jan. 15, 2009).
International Preliminary Report on Patentability, PCT/US2007/072217, 11 pages (Feb. 12, 2009).
International Preliminary Report on Patentability, PCT/US/2007/072209, 10 pages (May 14, 2009).
International Preliminary Report on Patentability, PCT/US/2007/078203, 13 pages (Mar. 26, 2009).
International Preliminary Report on Patentability, PCT/US/2007/078204, 11 pages (Apr. 2, 2009).
International Preliminary Report on Patentability, PCT/US/2007/078205, 10 pages (Mar. 26, 2009).
International Preliminary Report on Patentability, PCT/US/2007/078207, 10 pages (Mar. 26, 2009).
International Preliminary Report on Patentability, PCT/US08/52943, 7 pages (Oct. 15, 2009).
International Preliminary Report on Patentability, PCT/US2007/072217, 11 pages (Feb. 12, 2009).
International Preliminary Report on Patentability, PCT/US2007/072209, 10 pages, (May 14, 2009).
International Preliminary Report, PCT/US2005/002484, 9 pages (Aug. 3, 2006).
International Search Report and Written Opinion for International Application No. PCT/US2006/025201, 18 pages (Jan. 29, 2007).
International Search Report and Written Opinion, PCT/US08/500346, 12 pages (May 22, 2008).
International Search Report and Written Opinion, PCT/US08/52943, 8 pages (Sep. 26, 2008).
International Search Report and Written Opinion, PCT/US2007/072202. 17 pages (Mar. 25, 2008).
International Search Report and Written Opinion, PCT/US2007/078204, 14 pages (May 15, 2008).
International Search Report and Written Opinion, PCT/US2007/078203, 15 pages (May 13, 2008).
International Search Report and Written Opinion, PCT/US2007/078205, 13 pages (Sep. 11, 2007).
International Search Report and Written Opinion, PCT/US2007/078207, 13 pages (Apr. 7, 2008).
International Search Report and Written Opinion, PCT1US2007/078205, 13 pages (Sep. 11, 2007).
International Search Report, PCT /US2007 /072217, 20 pages (Mar. 31, 2008).
International Search Report, PCT/US2006/025201, 12 pages (Feb. 7. 2008).
International Search Report, PCT/US2007/072209, 18 pages (Apr. 25, 2008).
International Search Report, PCT/US2007/072217, 20 pages (Mar. 31, 2008).
Japanese Office Action, Application No. 2004-508,669, (with English summary), 9 pages (Aug. 3, 2009).
Japanese Office Action, Application No. 2004-508,670, (with English summary), 13 pages (Apr. 21, 2009).
Vidacare Corporation Comments to Intraosseous Vascular Access Position Paper, Infusion NursesSociety, 6 pages (May 4, 2009).
Liakat A. Parapia, Trepanning of trephines: a history of bone marrow biopsy, British Journal of Haematology, pp. 14-19 (2007).
Michael Trotty, ""Technology (A Special Report)—The Wall Street Journal 2008 Technology Innovation Awards—This years winners include: an IV alternative, a better way to make solar panels, a cheap, fuel efficient car and a better way to see in the dark"", The Wall StreetJournal, Factiva, 5 pages (2008).
Notification of the First Chinese Office Action, Application No. 200580003261.8, 3 pages (Mar. 21, 2008).
Office Action for Canadian application 2,612,483, mailed Dec. 27, 2013.
Office Action for Chinese application 201210169546.0, mailed Apr. 18, 2014.
Office Action for Taiwanese application 093134480, dated Feb. 11, 2011.
Office Action in Canadian Patent Application No. 2,612,483, mailed Aug. 22, 2014.
Office Communication in European Application No. 08021732.6, dated Jul. 20, 2013.
Official Action for European Application No. 03756317.8, 4 pages (Dec. 28, 2006).
PCT Preliminary Report on Patentability, PCT/US/2008/050346, 8 pages (Jul. 23, 2009).
"Pediatric Emergency, Intraosseous Infusion for Administration of Fluids and Drugs,www.cookgroup.com, 1 page (2000)."
Pediatrics, Official Journal of the American Academy of Pediatrics, "2005 American Heart Association Guidelines for Cardiopulmonary Resuscitation and Emergency Cardiovascular Care of Pediatric and Neonatal Patients: Pediatric Advanced Life Support", Downloaded from www.pediatrics.org, Feb. 21, 2007.
Richard Cummins et al, "ACLS-Principles and Practice", ACLS-The Reference Textbook, American Heart Association, DD. pp. 214-218 (2003).
Riley et al., "A Pathologist's Perspective on Bone Marrow Aspiration Biopsy: I. Performing a Bone Marrow Examination,"Journal of Clinical Laboratory Analysis 18, pp. 70-90 (2004).

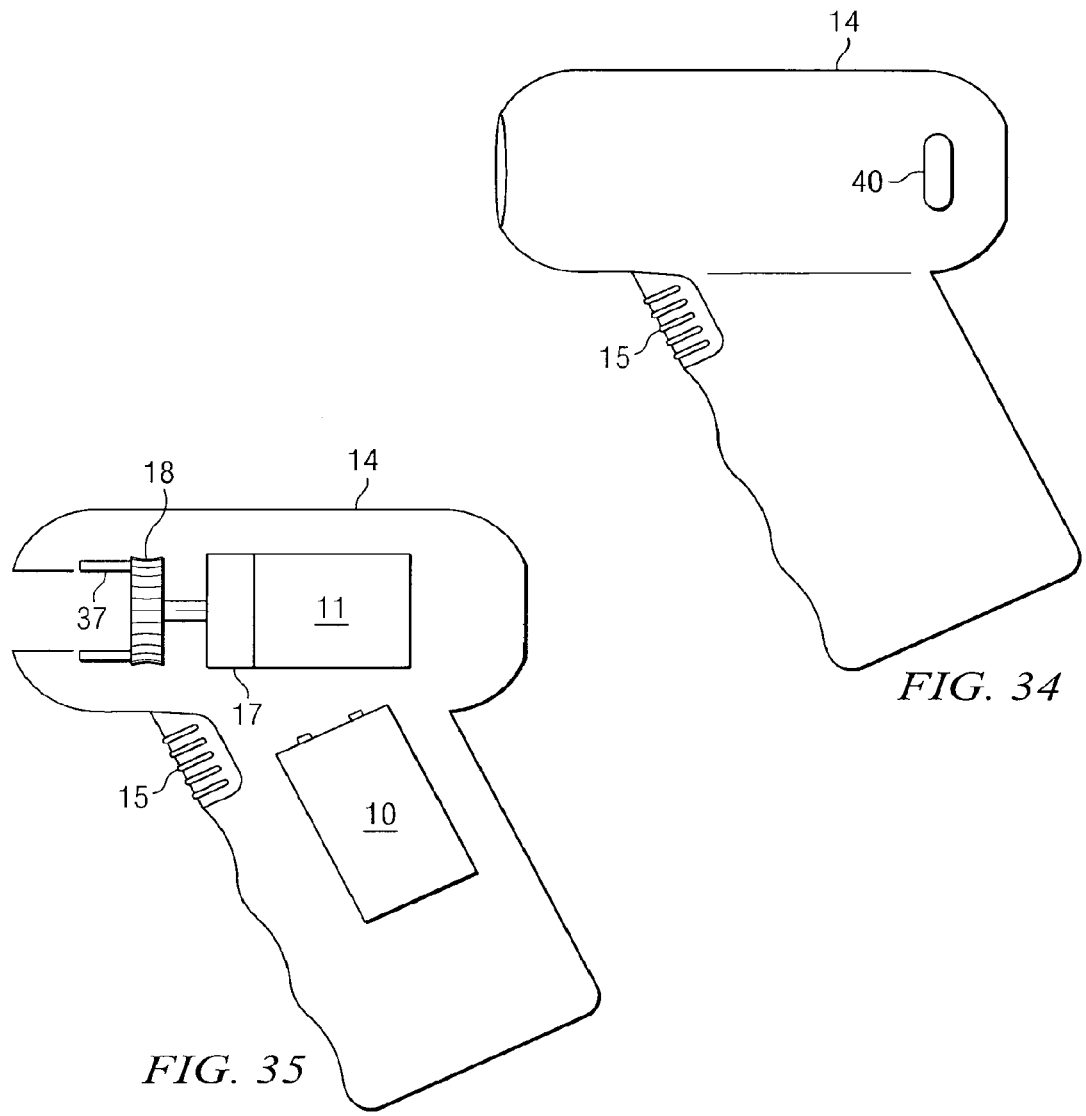
FIG. 34
FIG. 35
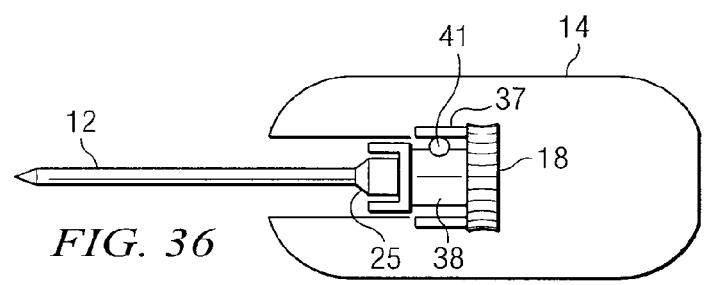
FIG. 36

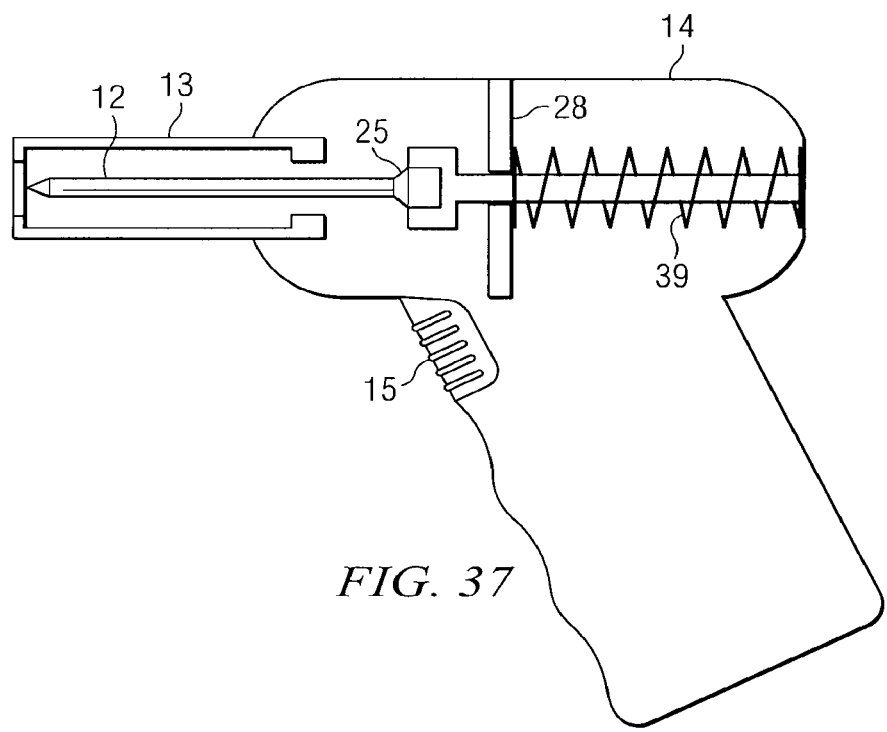
*FIG. 37*
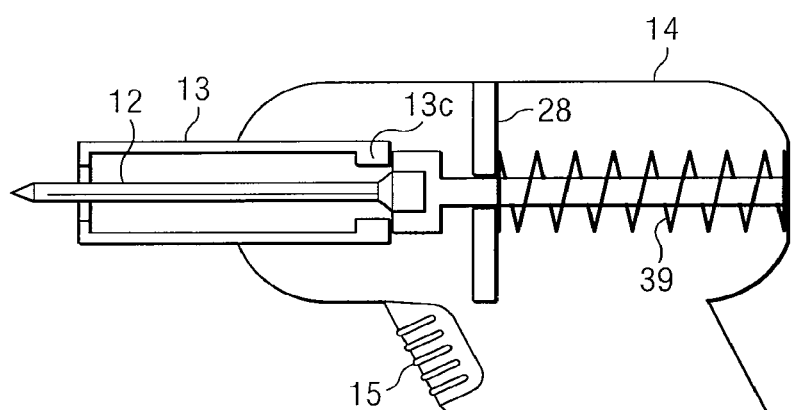
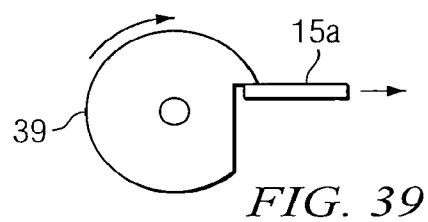
*FIG. 39*
*FIG. 38*

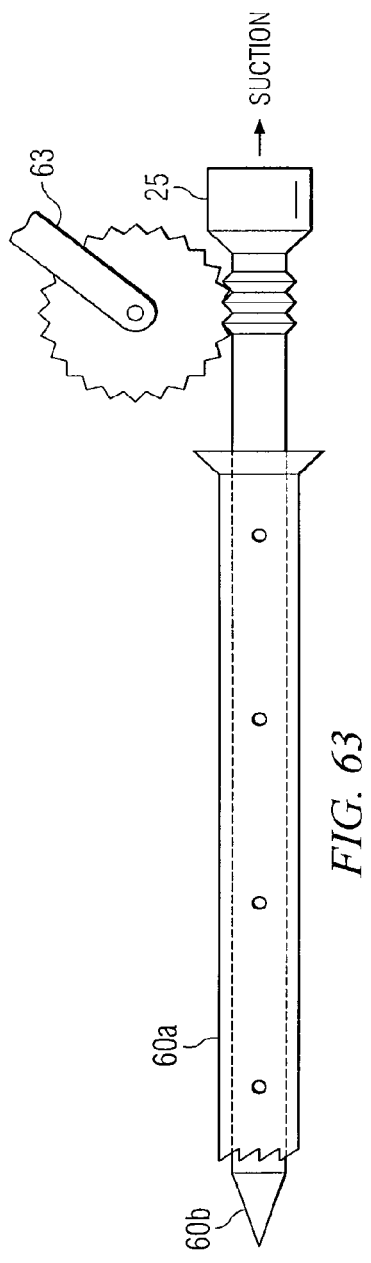
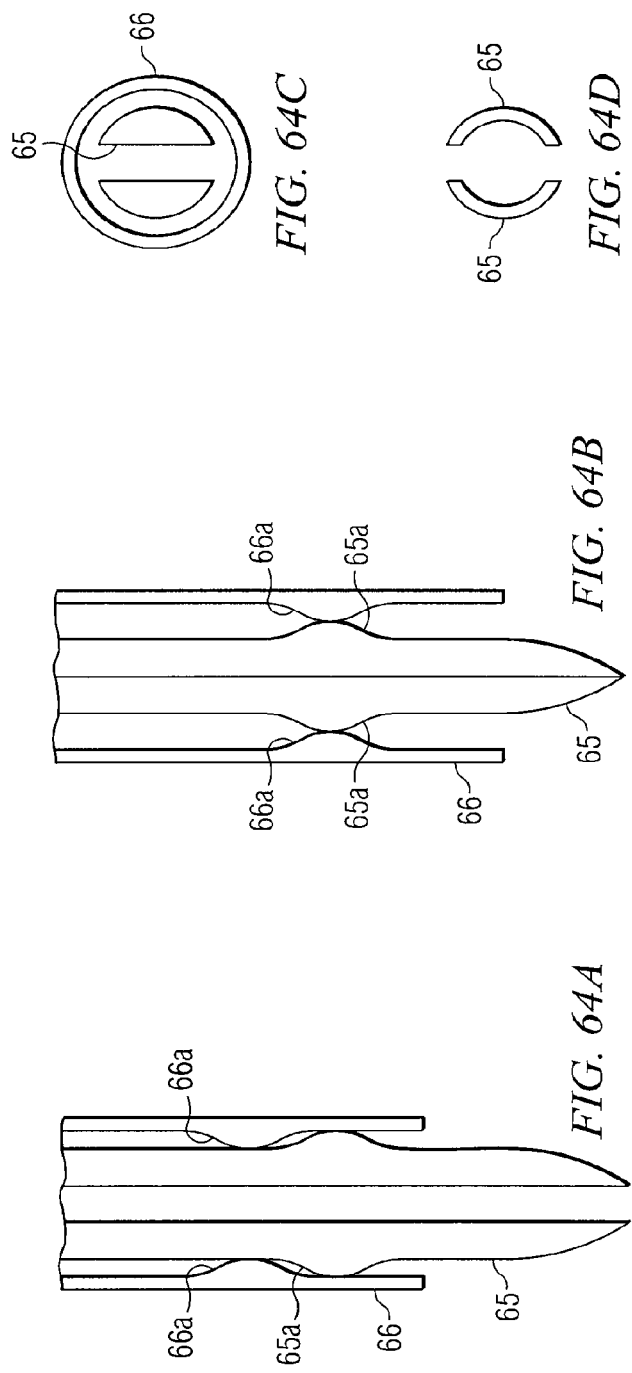
FIG. 63
FIG. 64A
FIG. 64B
FIG. 64C
FIG. 64D

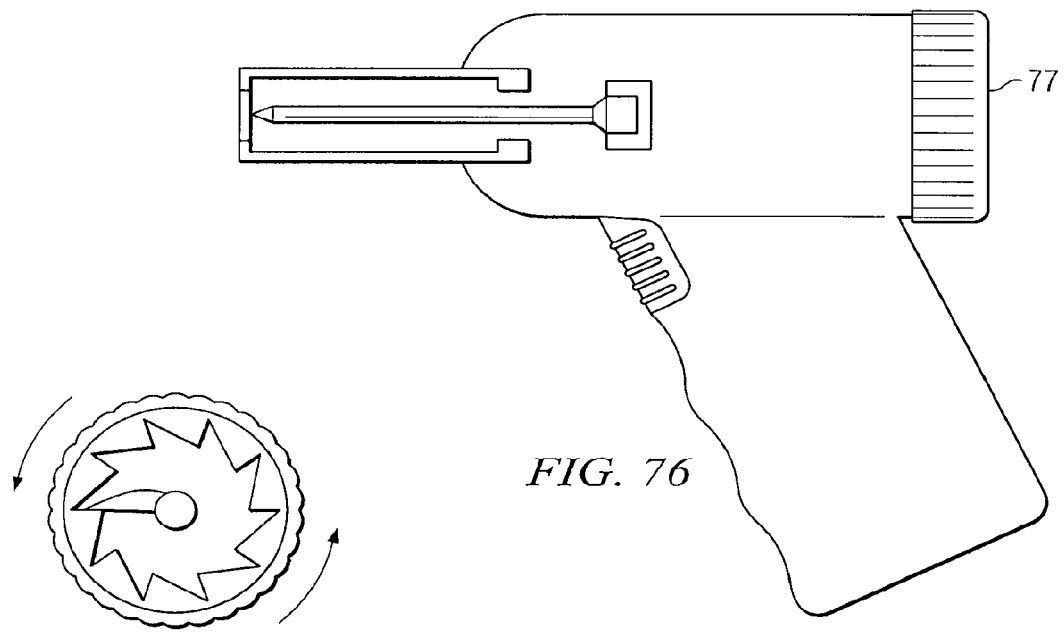
FIG. 76
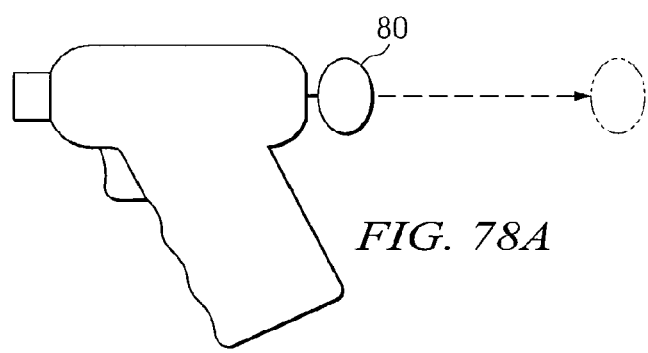
FIG. 77
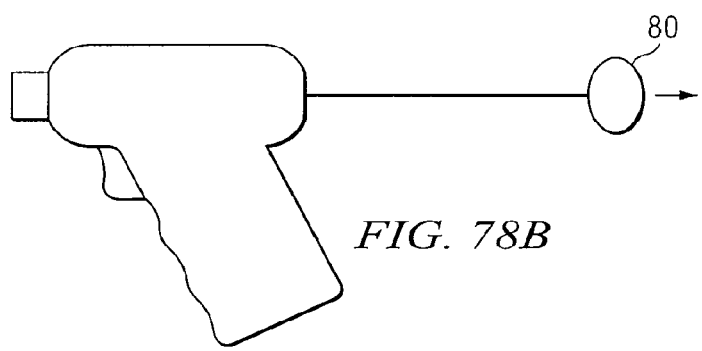
FIG. 78A
FIG. 78B

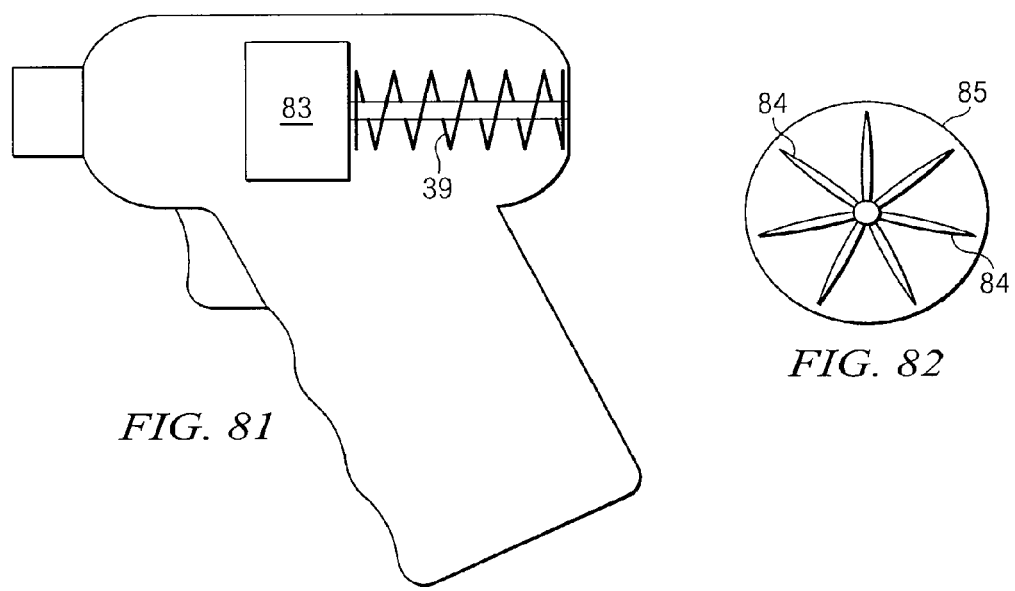
FIG. 81
FIG. 82
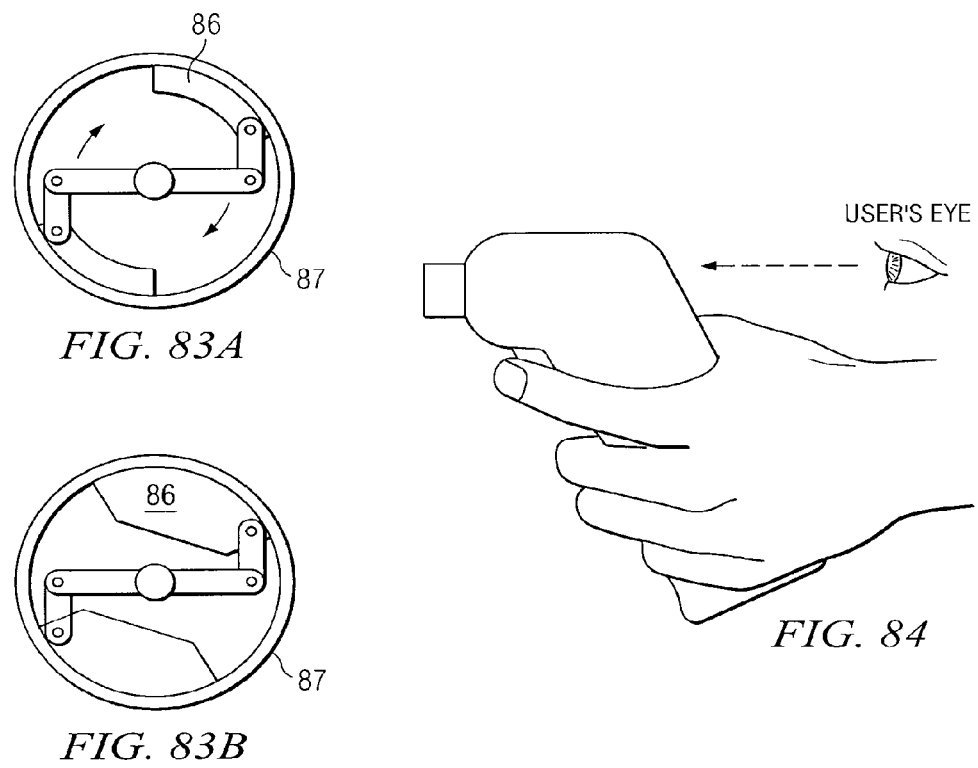
FIG. 83A
FIG. 83B
FIG. 84

APPARATUS AND METHOD TO PROVIDE EMERGENCY ACCESS TO BONE MARROW

RELATED APPLICATION

This application is a divisional of U.S. patent application Ser. No. 14/271,144 filed May 6, 2014, which is a divisional of U.S. patent application Ser. No. 12/331,979 filed Dec. 10, 2008, which is a Divisional of U.S. patent application Ser. No. 10/449,503, filed May 30, 2003, entitled "APPARATUS AND METHOD TO PROVIDE EMERGENCY ACCESS TO BONE MARROW," which claims priority to U.S. Provisional Patent Application Ser. No. 60/384,756, filed May 31, 2002, entitled "APPARATUS AND METHOD TO ACCESS BONE MARROW." The entire contents of each of the above-referenced disclosures are specifically incorporated herein by reference without disclaimer.

This application is co-pending to patent application entitled, "Apparatus and Method to Access the Bone Marrow for Oncology and Stem Cell Applications", Ser. No. 10/448,650, filed May 30, 2003; and co-pending to patent application entitled "Apparatus and Method to Access Bone Marrow", Ser. No. 10/449,476, filed May 30, 2003, which claim priority from the same provisional application.

TECHNICAL FIELD

The present invention is related in general to a medical device to access the bone marrow and specifically to an apparatus and method for penetrating the bone marrow with a powered drill and inserting a penetrator or needle.

BACKGROUND OF THE INVENTION

Every year, millions of patients are treated for life-threatening emergencies in the United States. Such emergencies include shock, trauma, cardiac arrest, drug overdoses, diabetic ketoacidosis, arrhythmias, burns, and status epilepticus just to name a few. For example, according to the American Heart Association, more than 1,500,000 patients suffer from heart attacks (myocardial infarctions) every year, with over 500,000 of them dying from its devastating complications.

An essential element for treating all such emergencies is the rapid establishment of an intravenous (IV) line in order to administer drugs and fluids directly into the circulatory system. Whether in the ambulance by paramedics, or in the emergency room by emergency specialists, the goal is the same—to start an IV in order to administer life-saving drugs and fluids. To a large degree, the ability to successfully treat such critical emergencies is dependent on the skill and luck of the operator in accomplishing vascular access. While it is relatively easy to start an IV on some patients, doctors, nurses and paramedics often experience great difficulty establishing IV access in approximately 20 percent of patients. These patients are probed repeatedly with sharp needles in an attempt to solve this problem and may require an invasive procedure to finally establish an intravenous route.

A further complicating factor in achieving IV access occurs "in the field" e.g. at the scene of an accident or during ambulance transport where it is difficult to see the target and excessive motion makes accessing the venous system very difficult.

In the case of patients with chronic disease or the elderly, the supply of easily-accessible veins may be depleted. Other patients may have no available IV sites due to anatomical scarcity of peripheral veins, obesity, extreme dehydration or previous IV drug use. For these patients, finding a suitable site for administering lifesaving drugs becomes a monumental and frustrating task. While morbidity and mortality statistics are not generally available, it is known that many patients with life-threatening emergencies have died of ensuing complications because access to the vascular system with life-saving IV therapy was delayed or simply not possible. For such patients, an alternative approach is required.

SUMMARY OF THE INVENTION

In accordance with teachings of the present invention, an apparatus and method are provided to allow rapid access to the bone marrow so that drugs and fluids can be infused into the circulatory system.

One aspect of the present invention includes an apparatus and method that will quickly puncture a bone with minimal trauma to the surrounding tissues and place a needle directly into the bone marrow to allow infusing drugs and fluids into the bone marrow.

One embodiment of the present invention includes a device that is a hand-held, battery-operated device that supplies rotational force to a needle in order to penetrate the bone marrow. In another embodiment of the present invention it is powered by means of a spring which can be rewound or by other mechanical means that do not include an electrical or battery power source. A spring-loaded driver may be used to wind up a spring as a power source to rotate the needle because it is cheap, reliable and has a long shelf life. One embodiment of a spring-powered device may include various mechanisms for modulating the speed of needle rotation.

Another embodiment of the invention calls for it to be reusable or disposable. In some embodiments the device itself may be reusable and the tissue penetrator or needle is disposable. A needle cover or shield can be incorporated into all embodiments.

In yet another embodiment of the invention, a unit dose of medication can be attached or incorporated into the device by means of a proprietary connection.

In the embodiments mentioned above, the intraosseous needle can be stabilized, once inserted, by means of a shield and a VELCRO strap.

In another embodiment of the invention, the device can be adapted to remove a specimen of tissue from the bone marrow (a bone marrow biopsy). In this embodiment a needle with three holes may be used to aspirate three different sites in the bone marrow.

In yet another clinical embodiment the device can be used to place an intracranial probe for pressure monitoring into the brain. In this embodiment there can be a two-way flow of fluids into or out of the brain depending on the clinical situation.

In the various embodiments listed, different sizes of the device and/or the needle are to accommodate different patient sizes or adult and pediatric sizes.

Various embodiments of the device can be configured for ergonomic comfort and ease of use. Alternate configurations of the motor-needle interface which may be required to achieve an ergonomic design include a flexible shaft or a 45 degree gear arrangement between the motor and the needle.

One embodiment of the present invention includes a device that may rapidly penetrate bone tissue and includes a fluid reservoir, which may be connected through an external port to a source of intravenous fluid. Another embodiment of the present invention includes a device for rapid penetration of bone, which may be used to directly insert a needle into a patient's bone marrow and then be disconnected from the needle. This allows a source of intravenous fluids to be connected to the needle that is positioned in the bone marrow. Still another embodiment of the present invention includes a device for rapid penetration of bone tissue having one or more fluid reservoirs that may be removed and exchanged with pre-filled drug ampules or fluid reservoirs.

In an alternate embodiment, the needle is operable to be detached from the hand-held housing after implantation such that the needle hub can be connected to an external source of drugs or medication. This feature may include a quick release mechanism. After detaching the needle from the device, a particular type of needle known as a "breakaway" needle may be implanted. The advantage to this type of needle is that it allows the insertion of a plastic intraosseous catheter into the bone marrow and removal of the surrounding needle. This may be advantageous because it would allow the fixation of the catheter to the skin with another more desirable apparatus that is stable and resistant to infection.

Technical benefits of the present invention include a device for rapid penetration of bone tissue that is portable and may be carried in the pocket or a portable emergency kit of a health care provider for emergency access to a patient's circulatory system.

Technical benefits of the present invention include obtaining access to the circulatory system that is fast, inexpensive and poses minimal risk to a patient.

An apparatus formed in accordance with teachings of the present invention may be used to quickly penetrate the outer layer of the bone so that drugs and fluids can be injected directly into the bone marrow.

The present invention provides an apparatus and method for use in emergency rooms, on the battlefield, in Emergency Medical Services settings, oncology treatment and veterinary applications.

Summary of Technical Benefits of Invention
  Hand Held
  Small size
  Intuitive human interface
  Similarity to other commercial and medical devices
  Battery Powered Motor
  Long shelf life (minimum 2 years)
  Off the shelf components, whenever possible
  Enough reserve power to function under wide range of temperature and torque conditions
  Spring Powered Motor
  Electrical Powered Motor
  Hollow Drill (Needle)
  Based on FDA approved needle design and materials
  Unique drilling tip with side ports
  Luer Lock for standard syringe and IV connection
  Stabilizing component i.e. silicone pad and/or securing wings
  Needle safety issues to comply with FDA and State requirements
  Safety-cover, contamination, and disposable factors included
  Depth control
  Disposable Version
  One time use
  Looks and feels disposable
  No significant regulatory concerns
  Designed not to be reused (locking mechanism self destructs etc.)
  Reusable Version
  Substantial driver
  Easy to connect needle and/or syringe (unit dose medication)
  Safety design to throw away parts
  Proprietary connector to prevent miss-use
  Significant Market Appeal
  Advanced industrial design
  Superior ergonomics (human interface design)
  Looks and feels safe
  Color, weight and sound attractive
  Reliable
  Power—rarely stalls, rarely fails
  Always functions (99 plus percent)
  Needles will not break or separate under normal use
  Tough enough to withstand dropping and abuse in EMS and military setting
  Automatic Detachable Mechanism
  No decision or action required
  When needle penetrates to proper depth, it will detach (release) from the driver
  Meets FDA 510 k Approval
  Similar (equivalent) to existing devices for the purpose of approval
  Unit Cost $25 for Some Models
  The lower the cost the better

BRIEF DESCRIPTION OF THE DRAWINGS

A more complete and thorough understanding of the present invention and advantages thereof may be acquired by referring to the following description taken in conjunction with the accompanying drawings, in which like reference numbers indicate like features, and wherein:

FIGS. 34-36 depict various views of a reusable driver.

FIG. 37 depicts a wind-up-spring powered intraosseous device.

FIGS. 38-40B depict the operation of the intraosseous device of FIG. 37.

FIG. 63 depicts a method of using an inner and an outer biopsy needle.

FIGS. 64A-64D depict a different set of inner and outer biopsy needles.

FIG. 76 depicts a different wind-up-spring powered intraosseous device.

FIG. 77-80B depict different mechanisms for winding a spring.

FIGS. 81-83B depict different mechanisms for controlling rotational speed.

FIG. 84 depicts a different intraosseous device.

DETAILED DESCRIPTION OF THE INVENTION

Figure 1:
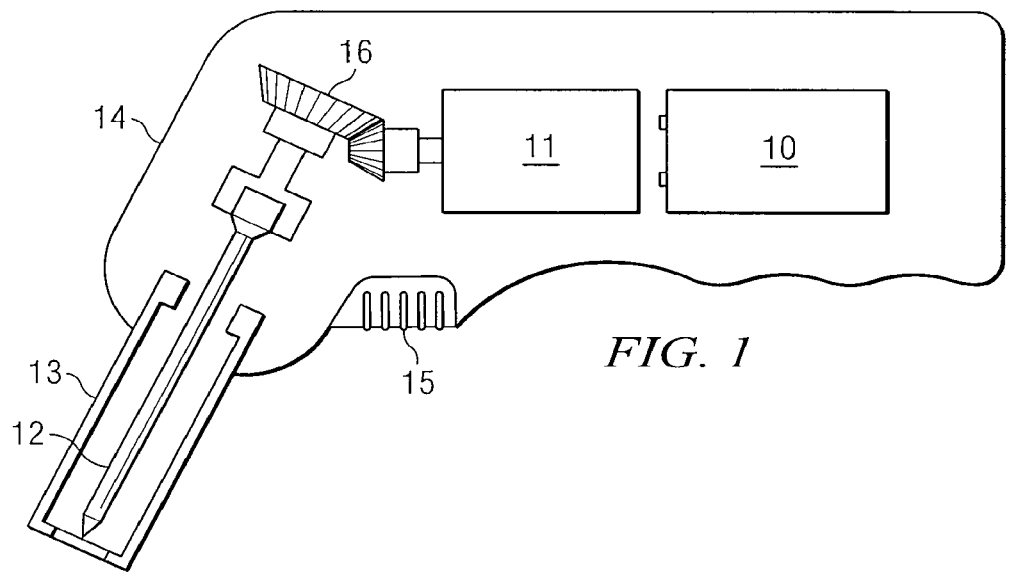
FIGS. 1-5B depict various devices for the rapid penetration of bone.
Figure 90:
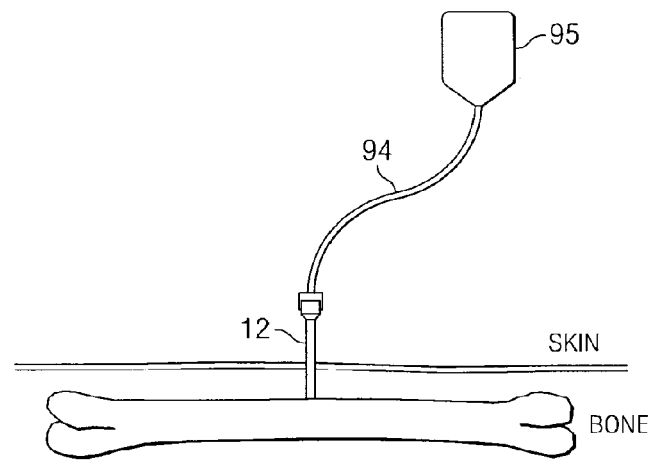
FIG. 90 depicts the operation of the intraosseous device of FIG. 87 with the connector of FIG. 89.

Preferred embodiments of the invention and its advantages are best understood by reference to FIGS. 1-90.

Although the present invention and its advantages have been described in detail, it should be understood that various changes, substitutions and alternations can be made herein without departing from the spirit and scope of the invention as defined by the following claims.

Configurations

FIG. 1 depicts a device for the rapid penetration of bone to provide IV access in an emergency. The device may include a portable power supply such as a battery 10, a motor 11, a needle or tissue penetrator 12, a retractable needle shield 13, and a housing 14. FIG. 1 shows a 45-degree angle of the needle axis from the driver (body) to enable the user to see the target site while the handgrip gives solid control. The trigger 15 is placed for natural use by the index finger. This configuration (angle) is made possible by the use of a 45-degree reduction gear 16. The gear also slows the speed of the drill while maximizing its power.

Figure 2:
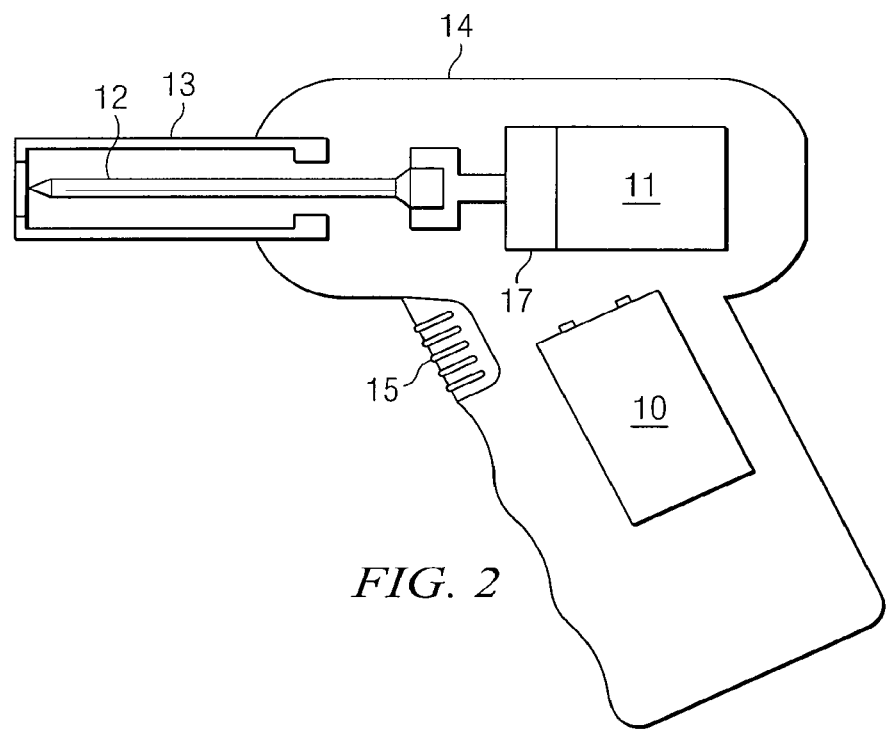

FIG. 2 depicts a familiar shape, much like a commercial hand drill, to give the user maximum control. The battery 10 is placed in the handle to enable a compact size. The use of an OEM gearbox 17 gives the needle the correct power and speed.

Figure 3:
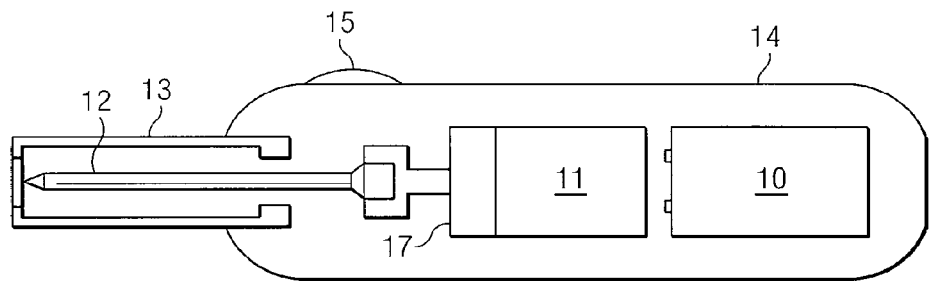

FIG. 3 uses a pen design with the trigger (switch) near the needle for better control. The motor and battery are aligned to provide a slim body.

Figure 4:
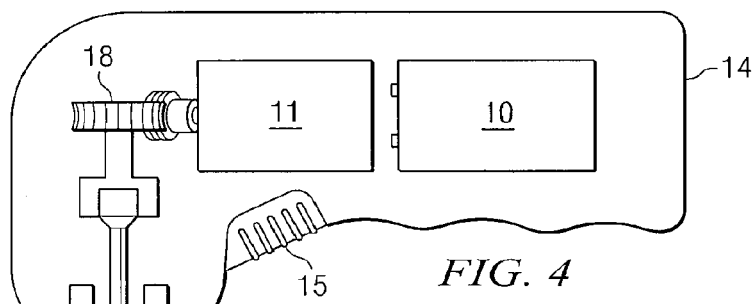

FIG. 4 depicts a 90-degree angle between the drilling assembly and the body of the VidaPen. This allows the use of a worm gear 18 for maximum power in hard bone applications and slower speed.

Figure 5A:
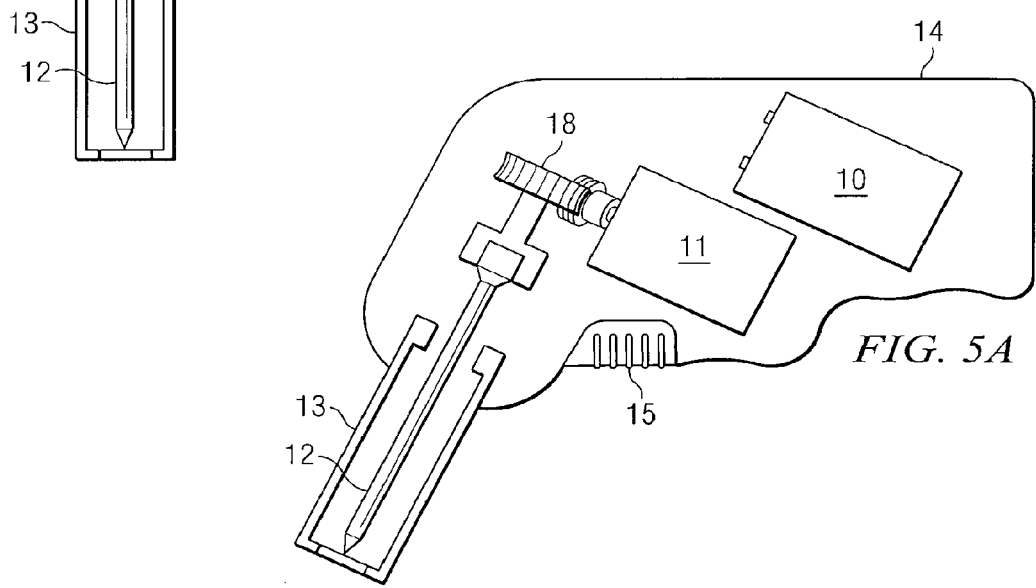

FIG. 5A shows a worm gear with the battery off-set to allow for a shorter configuration. The 45-degree angle between the handle and the driver gives the user better visualization of the target during use.

Figure 5B:
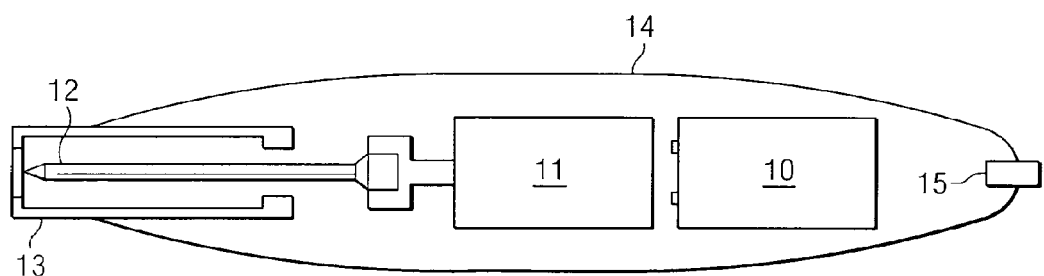

FIG. 5B depicts a slender configuration and a small size. It assumes the size and shape of a pen. This application is ideally suited for smaller bones i.e. in pediatrics and veterinary use where less power is needed and a smaller size permits quiet, unobtrusive use. The switch on this model can be on the end or along the side, as the user prefers.

These are only a few examples of the many configurations that are possible. The key is to design the driver for the best and most comfortable human (hand) interface, providing the best control and best visualization.

The body of the driver can be plastic, ABS, metal, or any other suitable material. Bearings can be metal, ceramic, plastic, ABS or any other suitable material.

The needle shield can be of any configuration as long as it provides protection to the user from being accidentally stuck by the needle, either before or after use. It will be retractable or removable. The driver can also stabilize the skin during the drilling process.

Switch (trigger) Manual Operation

The switch can be mechanical or electrical. It can be enclosed (to make it water proof) or exposed for easier use. Several embodiments are considered.

Figure 6:
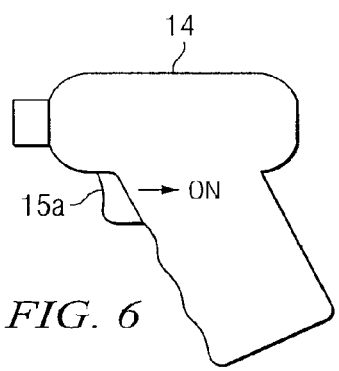
FIGS. 6-9 depict various manual switches.

FIG. 6 shows a sliding trigger 15a.

Figure 7:
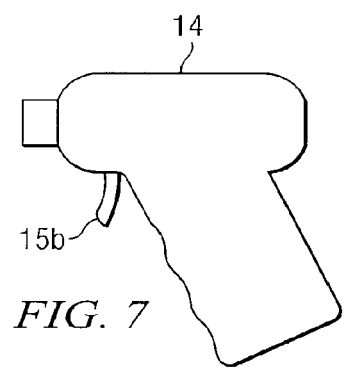

FIG. 7 shows a lever trigger 15b.

Figure 8:
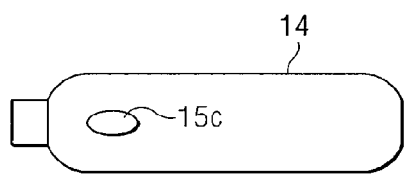

FIG. 8 depicts a button 15c.

Figure 9:
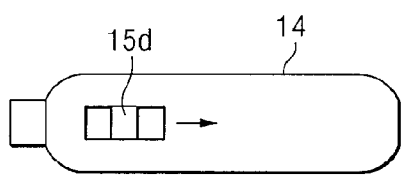

FIG. 9 depicts a slide switch 15d. This may be a lock open—lock closed arrangement or have a slide on and automatic shut off feature.

Switch (trigger) Automatic Operation

The switch may be activated by an event, such as the shield retracting or a deliberate action, such as the user pulling a pin, thus preventing accidental discharge and providing additional safety features.

Figure 10:
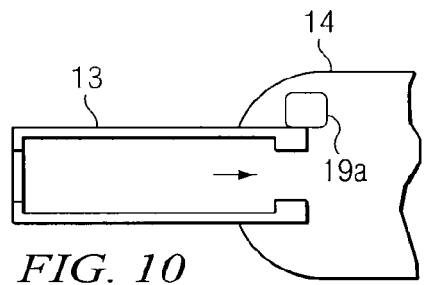
FIGS. 10-12 depict various automatic switches.

FIG. 10 shows a pressure sensor 19a (or other mechanical or electrical device) that will activate the motor when sufficient pressure is applied to the shield 13.

Figure 11:
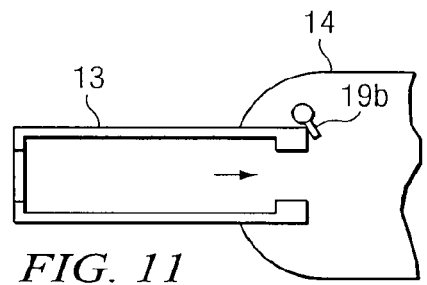

FIG. 11 shows an interior switch 19b, which is activated by movement of the shield 13, inward during the drilling procedure. This will allow (or require) the needle to penetrate the skin before it is able to rotate. This will assure that the skin and subcutaneous tissue will not wind up on the drill during rotation.

Figure 12:
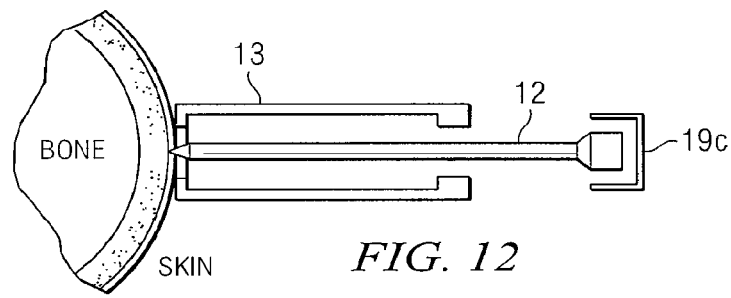

FIG. 12 shows a sensor 19c on the needle 12. This sensor can be set for a higher pressure than for the needle to penetrate the skin. Thus, when the needle is pushed sufficiently against the bone, the sensor will activate the motor. This control will ensure that the needle reaches the bone before it begins to rotate (drill). In this embodiment, the precise location of the needle tip can be controlled for accurate placement. From this known position, the needle can be directed (designed) to drill further into the bone to a set distance, i.e. one centimeter, thus eliminating the guesswork of determining the proper depth. This feature is important because the target area within the bone is reliable and predictable, whereas the distance from the skin to the bone is not predictable and varies considerably between patients depending on their size, weight, and fat distribution.

Control Depth of Penetration

In addition to FIG. 12 above, other methods of controlling the depth of needle penetration involve adjusting the shield covering the needle. The user will determine the proper depth from package inserts based on the patient's weight and height.

Figure 13:
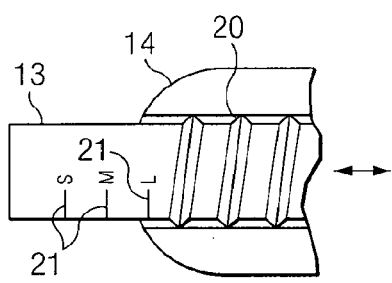
FIGS. 13-17 depict different depth control mechanisms.

FIG. 13 shows the depth of the penetration is adjusted by rotating shield 13 having threads 20 prior to use to the desired depth. Easy to read indicator marks 21 assure the proper setting.

Figure 14:
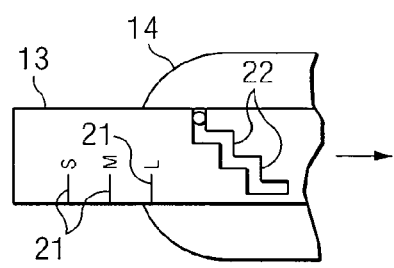

FIG. 14 depicts a stepwise adjustment, made by rotating shield 13 having notches 22 to the desired setting.

Figure 15:
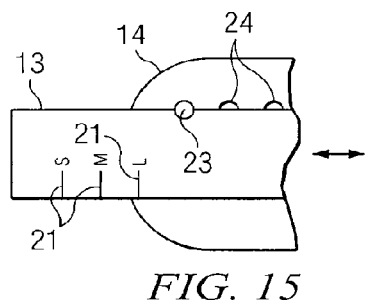

FIG. 15 shows the same adjustment made by clicking the shield into different desired depths shown by markings 21 on the outside. According to this embodiment, a ball 23 is fixed to shield 13 and may engage any of the detents 24 in housing 14.

Figure 16:
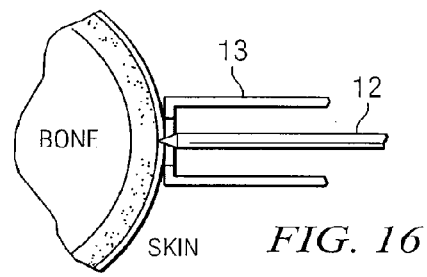

FIG. 16 depicts a manual method of determining accurate placement of the needle tip upon use. It requires the user to manually push the needle through the skin and against the bone prior to activating the trigger. This will assure that the penetration will be controlled from that point and can be set to a precise, predetermined depth. Upon pulling the trigger 15, needle 12 advances a pre-set distance (depth) into the bone.

Figure 17:
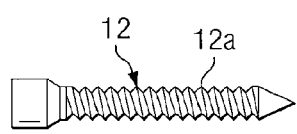

FIG. 17 depicts a "sure fast" type of IO needle, which has a threaded shaft 12a. In this case, counting the revolutions with a stepper motor or a shaft encoder controls depth of needle placement. Parameters of depth can be controlled based on the size and weight of the patient. Depth can also be computer controlled and would be more precise.

Release Mechanism (Needle from the Driver)

A well-designed release mechanism is necessary to assure worry free operation of the device. Ideally, the needle should separate from the chuck (holding mechanism) automatically upon proper penetration and depth of the needle into the bone. Otherwise the user might accidentally withdraw the needle from the bone while taking away the driver. Additional steps to separate the trocar and the needle from the body (motor and driver) would introduce the possibility of error and require greater skill levels to properly use the device. Therefore a trouble free chuck is required. It must be sturdy and proprietary to prevent miss-use.

Figure 18:
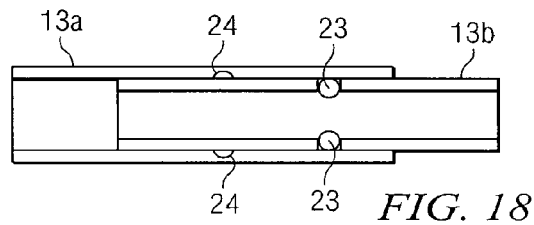
FIG. 18 depicts a mechanism for securing and releasing a needle.

FIG. 18 shows a standard "Sears" chuck release mechanism. The outer sleeve 13a is spring loaded and ball bearings 23 on inner sleeve 13b hold the target device (IO needle; not expressly shown) in place.

Figure 19:
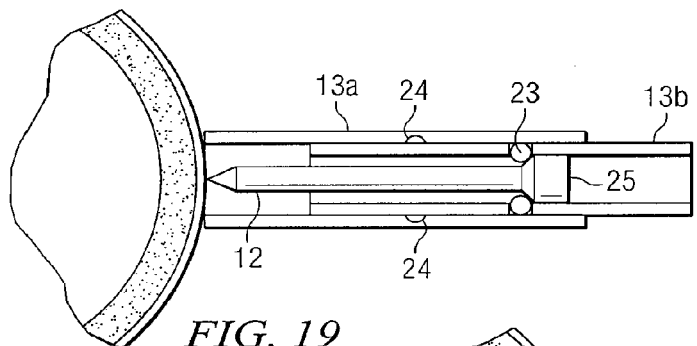
FIGS. 19 and 20 depict the operation of the mechanism in FIG. 18.

FIG. 19 shows the chuck with the VidaPen IO needle 12 in place. Ball bearings 23 engage and hold in place Luer lock 25.

Figure 20:
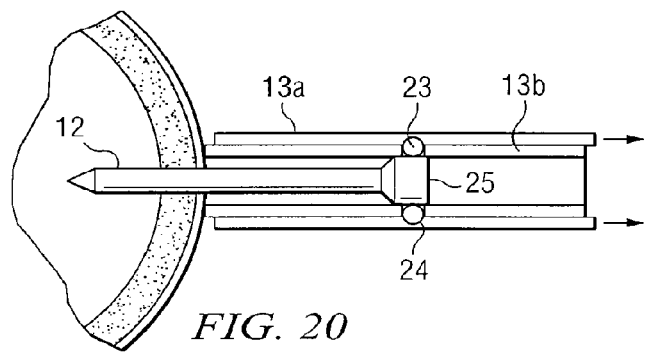

FIG. 20 shows the IO needle 12 penetrating into the bone. When the outer sleeve 13a slides to the preset position, the holding balls 23 fall into the detents 24 and the needle 12 (Luer lock 25) is released.

Figure 21:
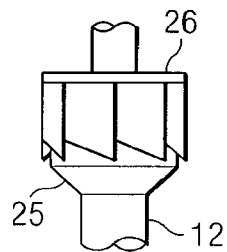
FIG. 21 depicts a different mechanism for securing and releasing a needle.

FIG. 21 shows a proprietary chuck (clamp, holder 26). This unit represents the female Luer lock 25, which will securely hold the needle 12 during the drilling phase of the operation.

Figure 22:
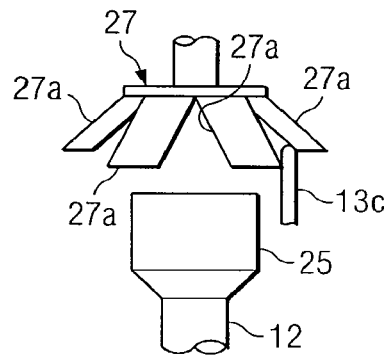
FIGS. 22-24 depict the operation of the mechanism in FIG. 21.

FIG. 22 shows the chuck 27, which is made to break away (unclamp, release the needle) when triggered by an action, such as a retractable shield rod 13c from the shield striking the rotating chuck. The rotating action of the motor (and the needle unit) provides the inertia (power) to break the chuck and release the needle. There are several configurations that will accomplish this action. This figure shows a series of wings 27a held together during manufacturing but when struck by the rod (trigger) will separate the chuck in at least two places, thus freeing the needle 12 to slip out of the unit. In essence the chuck will self-destruct.

Figure 23:
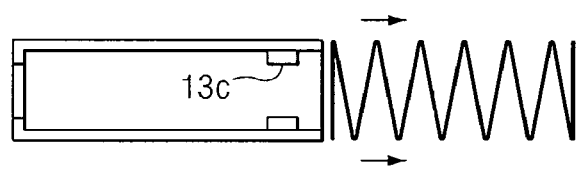

FIG. 23 shows how the shield 13 is spring-loaded and slides into the body of the driver with pressure and the attached rod 13c (trigger) moves toward the target point on the chuck to release it.

Figure 24:
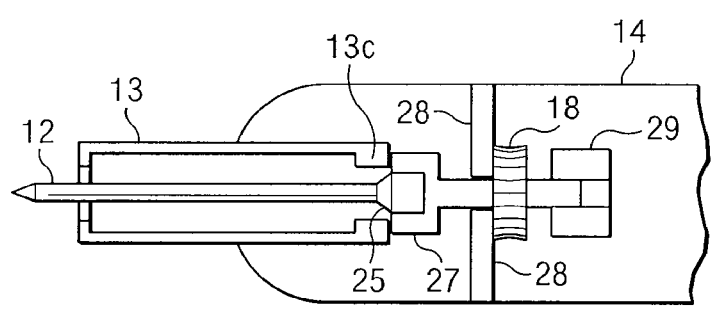

FIG. 24 further shows the trigger 13c of the shield 13 hitting the chuck mechanism 27 (including the female portion of the Luer lock 25) in order to release the needle with its male portion of the Luer lock 25. Chuck 27 and needle 12 are rotatably attached to bearings 28 and 29.

Proprietary Needle Holder

In order for the VidaPen IO needle to be competitive in the market place, it must utilize a standard Luer lock mechanism. IV fluids and standard syringes use the Luer lock to function (connect to the needle) for giving drugs, fluids and blood. A Luer lock consists of a male portion (connected to the needle) and a female portion connected to the syringe or IV line. In order to protect VidaPen from competitors (misuse) the female Luer lock must be connected to the chuck (holding mechanism) of the driver by a proprietary design. The embodiment of this claim utilizes a key-and-lock mechanism for easy insertion and release.

Figure 25A:
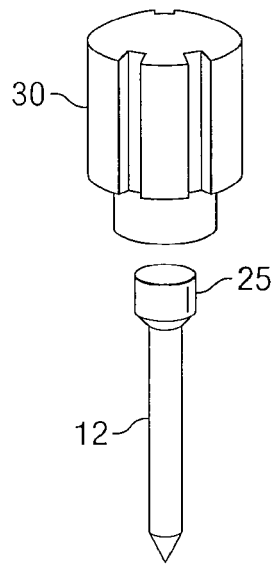
FIGS. 25A-25D depict a keyed cylinder for use in holding a needle.
Figure 25D:
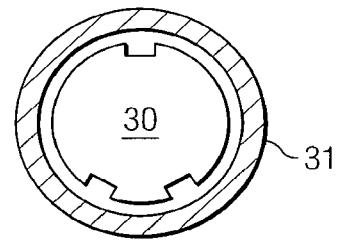
Figure 25B:
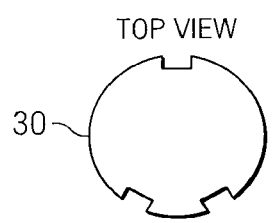
Figure 25C:
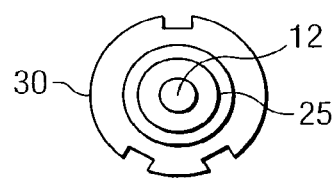

FIG. 25A shows the female Luer lock 25 being mounted onto a keyed cylinder 30. This key will mate with a similarly keyed chuck. FIG. 25B shows a top view of keyed cylinder 30. FIG. 25C shows a bottom view of keyed cylinder 30 with Luer lock 25 attached. FIG. 25D depicts a cross-sectional view of key 30 mounted in chuck 31. The key may take any shape, as long as it allows easy insertion and release from the chuck.

Reduction Gear for Power and Speed

In order to provide the power necessary to drill through the hardest bone, VidaPen's needle will need to have the required torque. It will be necessary to increase the torque provided by a small DC motor (or other motor i.e. $CO_2$ powered motor) by incorporating a gear into the drive train. Fortunately, most DC motors operate at high RPM and are thus suitable to be geared down. The needle's ideal rotational speed is slower than most OEM motors. Therefore, the gearbox (or gearing arrangement) will be ideal to slow the drill to optimum speeds.

Figure 26A:
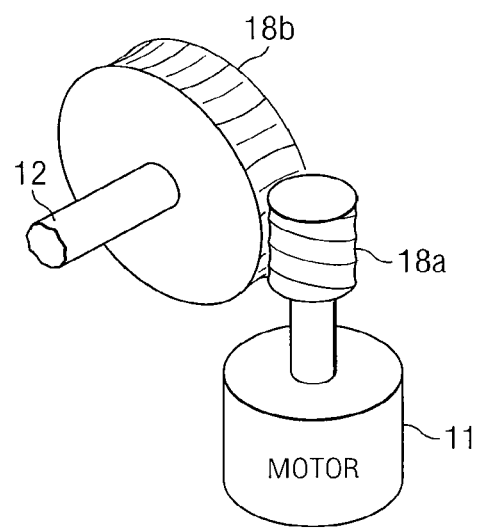
FIGS. 26A-26C depict different views of a worm gear drive.
Figure 26B:
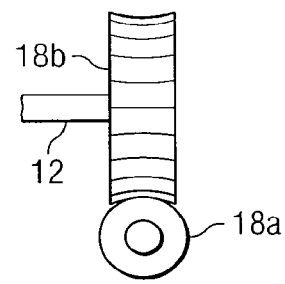
Figure 26C:
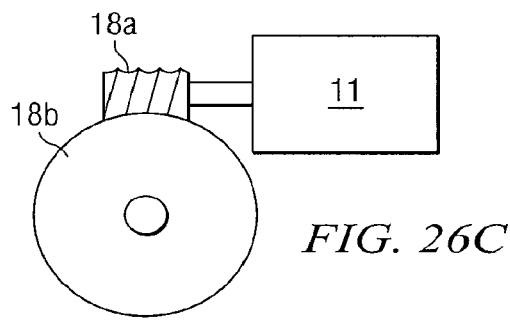

FIG. 26 shows isometric (26A), elevation (26B), and plan (26C) views of a VidaPen with a worm gear 18 for maximum power and slowest rotational speed.

Figure 27A:
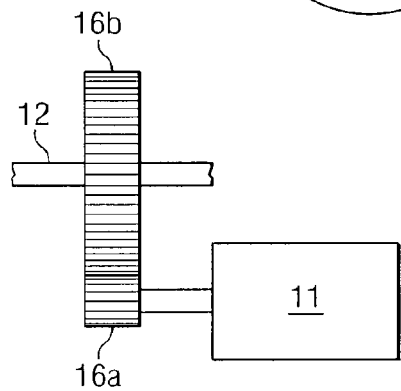
FIGS. 27A and 27B depict different gear drives.
Figure 27B:
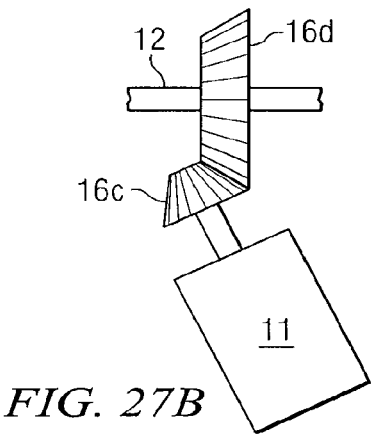

FIG. 27A depicts a reduction gear (reduction gear driver 16a and reduction gear 16b) for moderate power. FIG. 27B depicts an angled gear arrangement (driver 16c and reduction mitered gear 16d) so that the configuration of the handle and the needle (angle between the driver 11 and the needle assembly 12) can be more ergonomically correct.

Needle Tips (Cutting Surface)

Many types of cutting tips have been devised for bone drills. This design embodies the concept of using the outer needle and the inner trocar as a single unit for optimal penetration of bone with minimal disruption of the anatomy. This is important from the standpoint of keeping the side port open for injections and aspiration. In addition, this embodiment will allow for a tight fit between the needle and the bone for better fixation and prevention of leakage (extravasation).

Figure 28A:
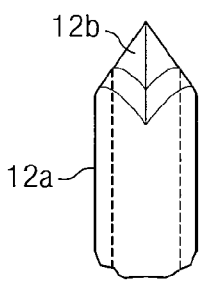
FIGS. 28A-28E depict different needle and trocar cutting tip configurations.
Figure 28B:
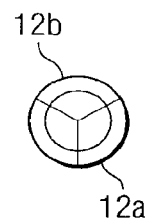
Figure 28C:
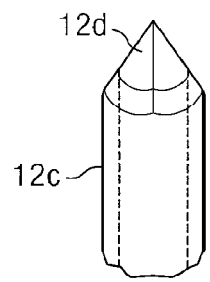
Figure 28D:
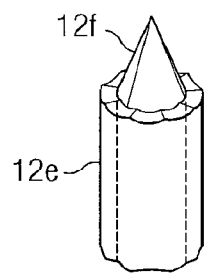
Figure 28E:
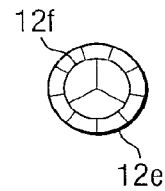

FIGS. 28A and 28B respectively show perspective and plan views of a triangular cutting tip incorporating the needle 12a and the trocar 12b as a single unit. The cutting tips of the trocar and needle are aligned. This will allow a smooth penetration of the skin prior to drilling the bone. FIG. 28C shows needle 12c and trocar 12d with aligned cutting tips for single cutting action. FIGS. 28D and 28E respectively show perspective and plan views of a triangular cutting tip configured such that needle 12e and trocar 12f cutting tips are not aligned to allow more cutting. The tips may be 45° or 120° out of phase. Two levels of cutting surface are provided with the trocar out of sync with the needle. The first enables the trocar to penetrate the bone with a sharp point and the second allows the needle to enlarge the hole with a chipping action.

Reusable Driver/Disposable Needle

One embodiment of the device calls for it being disposable. Another embodiment is designed for the body (driver) to be reusable and the needle to be disposable. This is made possible by providing a chuck that mates with a proprietary shaft attached to the needle's Luer Lock. The needles must maintain sterility during storage and mounting of the needle while the driver does not have to be sterile. The driver will be rugged in design and the battery (or other power source) will be rechargeable or the battery will be easy to replace with off-the-shelf batteries.

Figure 29:
FIG. 29 depicts a needle.

FIG. 29 depicts an IO needle 12 mounted on the female Luer lock 25. The Luer lock is attached to a keyed shaft 32, which snaps in place on the chuck of the VidaPen driver (not expressly shown).

Figure 30:
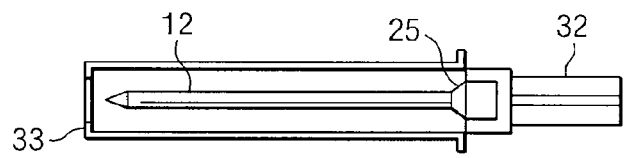
FIG. 30 depicts a needle with a removable cover.

FIG. 30 shows the removable needle cover (shield) 33 which is sealed during storage and mounting. The shield 33 provides a grip to better and safely allow the user to place the new needle 12 into the reusable driver.

Figure 31:
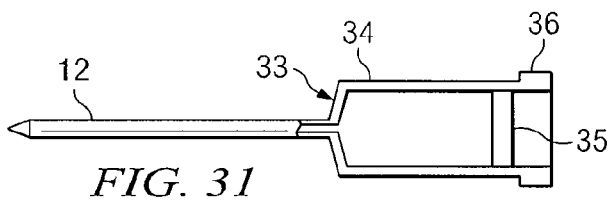
FIG. 31 depicts a unit dose cartridge.

FIG. 31 shows a disposable "unit dose" cartridge 33, which includes a pre-filled cylinder 34 and plunger 35, attached to a VidaPen IO needle 12. A clip 36 (configuration for a union) is incorporated into the cylinder 34 so that it can be easily mounted onto the drive mechanism of the body.

Figure 32:
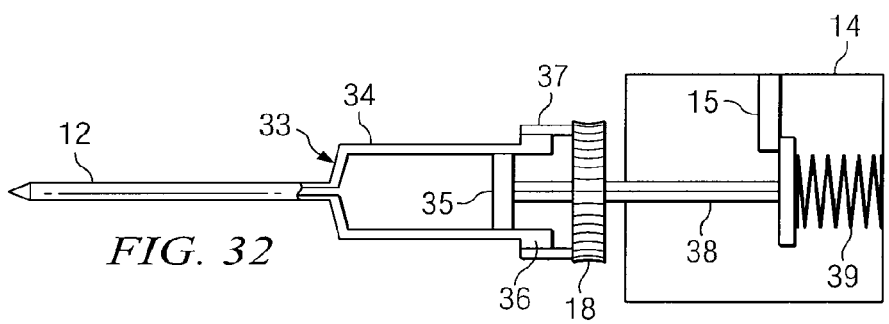
FIGS. 32 and 33 depict the operation of the unit dose cartridge in FIG. 31.

FIG. 32 depicts the "unit dose" ampule (cartridge 33 and needle 12) after it has been mounted in the driver. It has been mated with the chuck 37 of the driver. The chuck is attached to the rotator (driver) gear 18. Importantly, a grooved shaft 38 extends through the center of the gear so that it is free to slide in and out, while the gear is engaged and rotating. The shaft may rotate with the gear or may remain stationary with respect to rotation while the gear rotates around it. If it is stationary it will not need to be grooved. The shaft is spring loaded 39 and held in the cocked position by a trigger mechanism 15. The other end of the shaft rests against the "unit dose" plunger 35.

Figure 33:
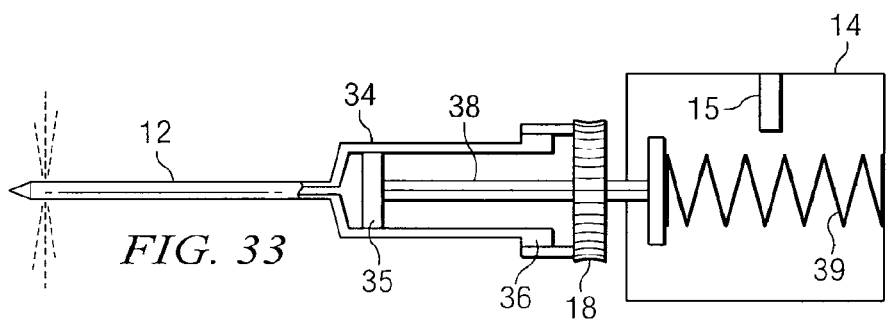

FIG. 33 upon release of the loaded spring 39 by a trigger mechanism 15, the shaft is propelled toward the "unit dose" plunger 35 and pushes the plunger 35 down the cylinder 34. By this action the fluid (drug) is injected through the distal orifices of the needle into the bone marrow.

FIG. 34 shows the configuration of the driver of the VidaPen without the needle 12 inserted. A battery indicator 40 is also shown.

FIG. 35 shows the motor 11, gearbox 17, and battery 10 of the reusable driver. It also shows the chuck 37, which is designed to accept the keyed needle or "unit dose" ampule. It is important in the reusable design to have a rechargeable battery or the ability to easily change off-the-shelf batteries i.e. a 9-volt battery. It may also incorporate a battery level indicator or other battery reserve indicator (not expressly shown).

FIG. 36 depicts the reusable driver (body, handle) with a disposable needle 12 mounted. In this embodiment the keyed shaft 38 is held in place in the chuck 37 with a spring ball 41. A clip or O-ring may also be used (not expressly shown). Thus, the needle may be snapped in place Spring Loaded Driver This embodiment uses a wind up spring as a power source to rotate the needle. This approach bypasses the inherent problems of motors: expense; reliability; weight; and size; and the limitations of batteries: size; weight; shelf life; reliability; decreased efficiency at low temperatures, and cost. Springs are cheap, reliable, long shelf life, small, low weight, predictable and operate well under a wide range of environmental conditions including heat and cold. The reason a wind-up-spring is an excellent choice for this application is because the VidaPen needle requires high torque for only a short period. The maximum time needed is less than 6 seconds, which translates into @100 revolutions. Further, a spring meets the requirements of high reliability under a wide range of circumstances. Motors and batteries can serve this purpose, however, it is a waste of resources and adds unnecessary complexity to have such a power source that is only required for 6 seconds.

FIG. 37 depicts the wind-up-spring version of the VidaPen. Rotation begins when the spring 39 is released by the trigger mechanism 15. The needle 12 is released, after seating in the bone, in the same way as it does in the motor/battery version.

FIG. 38 shows the preferred embodiment where rotation begins when the device senses the needle 12 is ready to penetrate the bone. This ideal position is sensed by retraction of the shield 13 into the driver or when sufficient pressure is applied to the needle 12 to trigger the release of the spring 39. This is important to assure the needle 12 is resting on the bone and sufficient pressure is being applied so that the rotation will not be spent (wasted) without addressing the intended target (the needle will spin only when its rotation will result in drilling into the bone).

FIG. 39 details how the manual trigger 15 will release the spring 39 and permit rotation of the needle (not expressly shown).

Figure 40A:
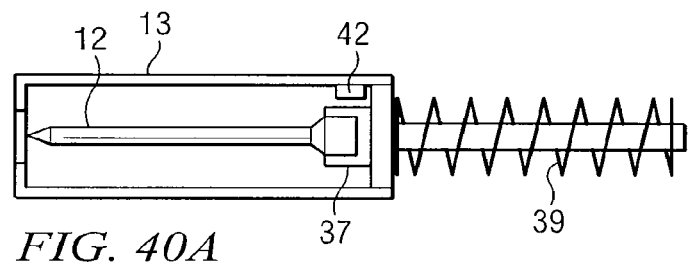
Figure 40B:
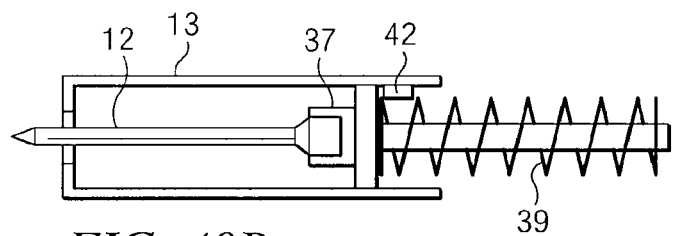

FIG. 40A shows how retraction of the shield 13 can be used to trigger the spring 39 release. In this case, a key 42 on the shield 13 holds the chuck from rotating. When the shield 13 is retracted the key 42 passes the notch in the chuck 37 (FIG. 40B), permitting the spring 39 to unwind and the needle 12 to rotate.

Figure 41:
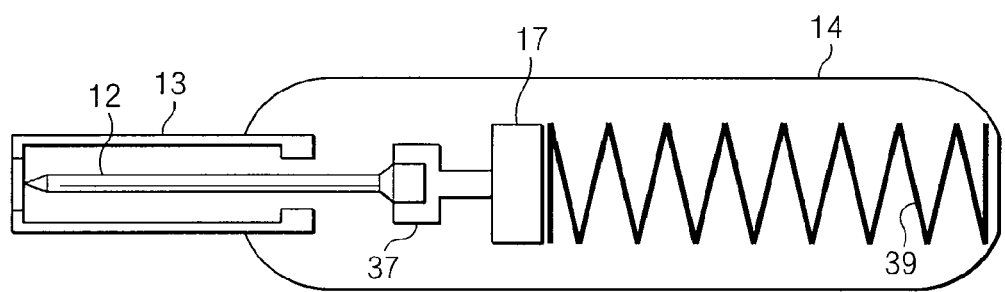
FIG. 41 depicts a different wind-up-spring powered intraosseous device.

FIG. 41 depicts a spring-powered device using a very powerful spring 39 (super spring). Such power enables more latitude in the design with respect to the total number of revolutions, rotational speed (rpm), and torque. This is accomplished by using a gearbox 17 to increase the torque (slow the speed) or decrease the torque (increase the speed). It should be noted that only 50 to 150 revolutions would be needed to accomplish the task of seating an IO needle in the tibia.

Paramedics, EMS, and the Military

Special uses for the VidaPen include operating in the field, where ruggedness and durability are of paramount importance. The device may be designed to be water proof, temperature resistant, crush proof and be made in different shapes and colors. In addition, the pre-hospital and combat situations are ideally suited to use the "unit dose" version (VidaPen II). That is because often what the medic needs is simply a one-time dose of medication, such as an antidote for poison or epinephrine, in order to stabilize the patient. Unit dose ampules are widely used by paramedics to give a predetermined amount of drug for a particular indication. There are a limited number of drugs needed to fulfill that need.

Figure 42A:
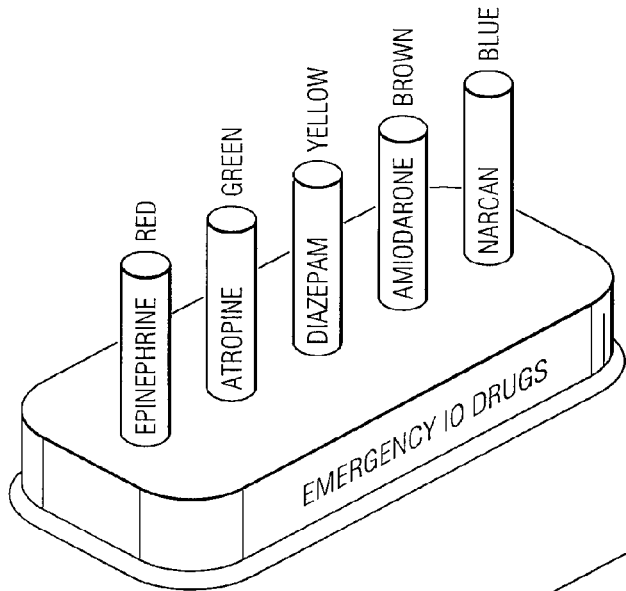
FIGS. 42A and 42B depict a set of drugs.
Figure 42B:
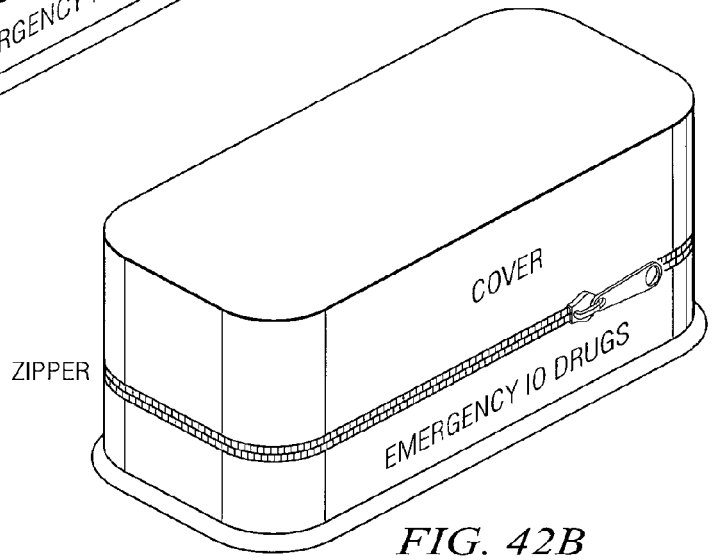

FIG. 42A shows a rack of single use (unit dose) VidaPen II that will meet most of the medic's immediate needs. These drugs are: Epinephrine (for cardiac arrest and life-threatening allergies); Narcan (for drug overdose); Atropine (for cardiac arrest and chemical exposures); Diazepam (for seizures and emergency sedation); and Amiodarone (for cardiac arrhythmias). It is envisioned that these drugs will be clearly labeled and color coded so they can be quickly and accurately selected in an emergency. As shown in FIG. 42B, the kit will contain all these drugs in an easy to carry and maintain pouch (stand). It will have a zip lock cover to protect it, but be easy to access in an emergency.

VidaPen I for Injecting Multiple Drugs and Fluids

VidaPen I is designed to provide rapid vascular access in less than 6 seconds.

Figure 43:
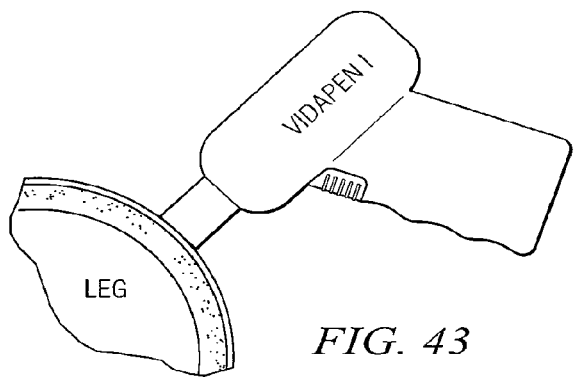
FIGS. 43-45 depict a use of an intraosseous device.

FIG. 43 the VidaPen I is placed on the target area just below the knee on the anterior tibia. This is an anatomical site that is easy to locate. This site is free from overlying vital organs or excessive subcutaneous tissue. The bone is typically close to the skin, except in the most obese. The target area is large, thus providing an ample margin of safety for correct placement. It is also a site that has the most positive clinical experience. Once the device is placed on the leg, pressure is applied and the needle will extend through the shield and penetrate the skin. The switch (trigger) is activated manually or automatically and the needle begins to drill the bone. The needle continues to advance to the predetermined depth, at which time it automatically detaches from the chuck and the driver (handle) is withdrawn, leaving the needle securely implanted in the bone.

Figure 44:
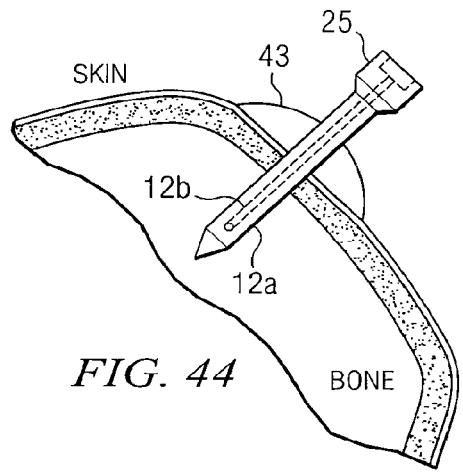

FIG. 44 shows the implanted needle 12a with the tip in the marrow and the exit port within the marrow cavity. The Luer lock 25 is further stabilized with a silicone (or other material) pad 43.

Figure 45:
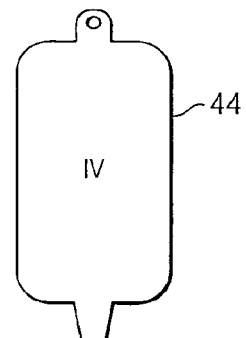
Figure 45:
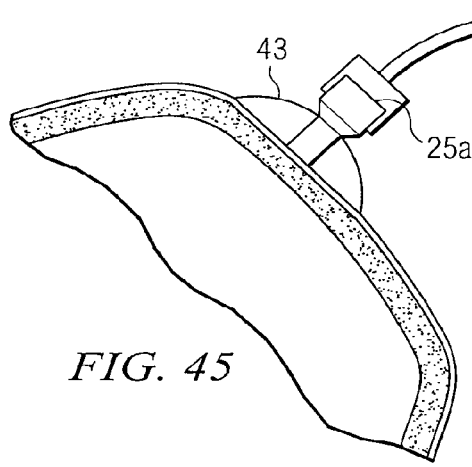

FIG. 45 shows the IO needle in place and secure. Standard Luer lock syringes 25a and/or IV tubing 25b are now connected to standard IV fluids 44 and infusion begins. Infusion may be by gravity or by pressure pump. Any drug or fluid that can be given IV can be given IO. When infusion is no longer required the needle is simply withdrawn and a band-aid is placed over the site.

Trocar

Drilling into bone with a hollow drill (needle) sometimes plugs the orifice and the side ports. To overcome that problem a trocar is often used. A trocar is a rod within the needle. It is removed after placement in the bone.

Figure 46A:
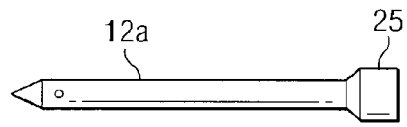
FIGS. 46A and 46B depict a needle with and without a trocar.
Figure 46B:
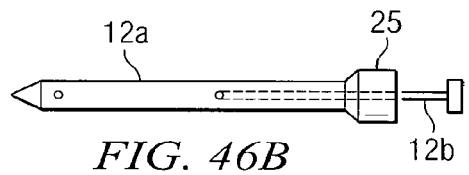

FIG. 46A shows an IO needle 12a being used without a trocar and FIG. 46B shows one being used with a trocar 12b. When a trocar is used, it becomes an integral part of the needle assembly and must engage the Luer lock 25 on one side and the chuck on the motor side. Thus, in all claims about the needle and the attachment of the needles to the motor (driver) the trocar is an integral part of the discussion.

Stabilizing the IO Needle

Stabilization of the IO needle is paramount for its success. Stabilization (how firmly the needle is seated in the bone) is affected by several factors including maintaining proper alignment during insertion (drilling). Other factors include: thickness and hardness of the bone; the length of the needle (longer needles are prone to rocking movements during use by virtue of their longer leverage arm); diameter of the hole during drilling compared to the diameter of the shaft at the point of seating (how loose or how tight a fit); smooth walled needle vs. threaded needle; and movement of the patient during use (causing rocking of the needle and subsequent loosening).

Figure 47:
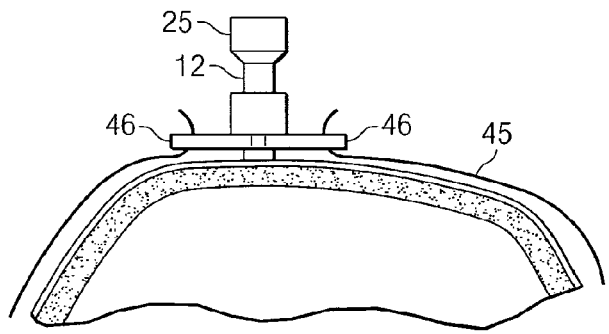
FIGS. 47-52 depict different mechanisms for stabilizing a needle after insertion.
Figure 48:
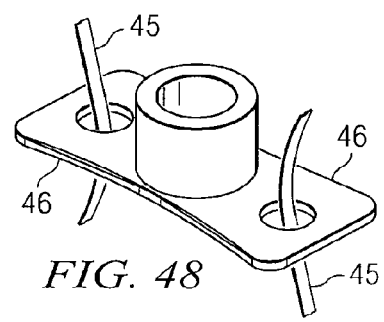

FIG. 47 shows the VidaPen IO needle in place. It has been secured to the leg by a strap 45 (cord, tape) and attached to the needle 12 via buckle 46 shown in FIG. 48 and placed around the leg to connect to the needle on the opposite side. This could be tied, snapped together by a buckle, or connected by another convenient method of attachment. The strap may have an adhesive surface to further stabilize the needle. The strap will prevent the needle from being accidentally removed or withdrawn and will keep it from excessive rocking and movement.

Figure 49:
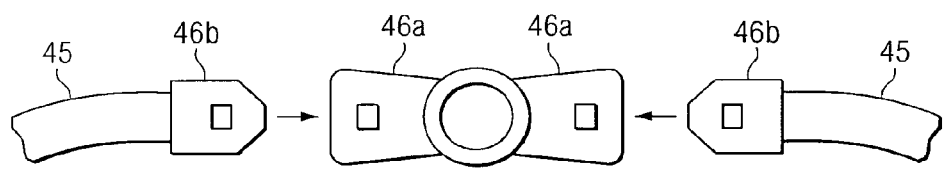

FIG. 49 shows a winged configuration of the needle with buckle attachments 46a on opposite sides. The buckle may be secured by inserting buckle tab 46b into buckle attachment 46a.

Figure 50:
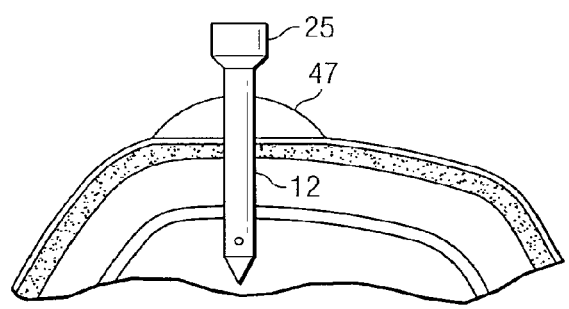

FIG. 50 shows the VidaPen IO needle 12 in place, seated in the bone, with a silicone (or other material) pad 47 resting between the base of the Luer lock 25 and the skin. This pad 47 will serve to stabilize the needle and keep it from excessive movement. It can be used with the attaching strap in FIGS. 48 and 49 above.

Figure 51:
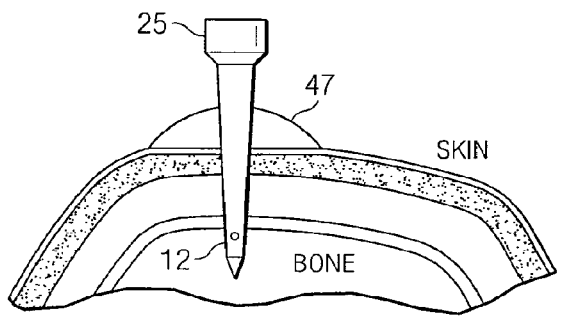

FIG. 51 is an exaggerated drawing, which shows how a slight taper to the diameter of the needle 12 could be used to provide a better or tighter fit to prevent extravasation. The increase in diameter as the needle is advanced in the bone must not be so great as to fracture the bone, but enough to provide greater seal and tightness.

Figure 52:
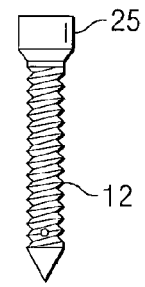

FIG. 52 shows the VidaPen IO needle 12 with a screw configuration (commonly called the "Sure Fast") which is known to provide a better seal.

Prevent and Manage Extravasation

The end result of a good seal between the needle and the bone is that fluid and drugs injected through the needle will flow into the circulatory system. The result of a broken seal (or loose seal) is that some of the fluid will extravasate (leak) into the surrounding tissues and may cause a compartment syndrome. This condition is one of the most frequent complications of IO use and one of the most serious. In the compartment syndrome pressure from the leaking fluid builds up in the leg (which has limited capacity for expansion) and cuts off the circulation to the foot. Therefore, precaution must be taken to prevent this complication and health providers must monitor their patients for the development of extravasation. This problem has never been adequately addressed by current manufactures of IO needles.

Figure 53:
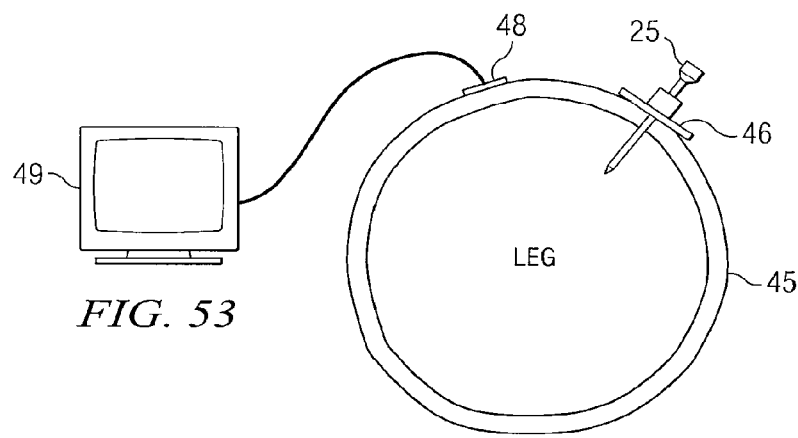
FIG. 53 depicts a strap with a sensor.

FIG. 53 shows the VidaPen IO needle 12 seated in the bone and connected to a strap 45 that is placed around the leg. The strap 45 is fitted with a sensor 48 that measures the pressure and/or the size of the leg. This strap 48 also serves as a stabilization device as in FIG. 47 above. When the sensor detects a preset increase in size or pressure, alarms are sounded. The sensor is operably coupled to a monitor 49 (computer) and may also be programmed to stop the infusion of fluid when it detects a rise in these parameters. Software and hardware to accomplish this feature are included in this claim.

Figure 54:
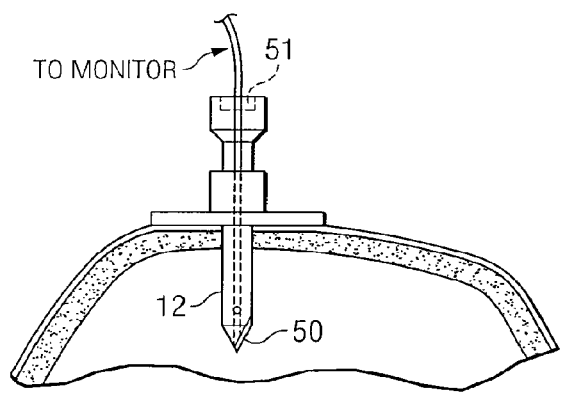
FIG. 54 depicts a needle with a sensor.

FIG. 54 shows a needle 12 in the bone that is equipped with a pressure transducer 50 in the tip that can measure intraosseous pressure. Another version is a similar needle placed in the muscle of the leg to similarly measure intra-compartment pressure. In the intraosseous version, a seal 51 (may be a valve or other method to isolate the transducer wire from the needle) is provided so that infusions of fluids may proceed while, at the same time, measuring the pressure at the tip of the needle. Measurements from the sensor may be analyzed by a computer, which will manage the problem (pre-set increase in pressure) by controlling the rate of infusion or stopping it all together and alarming the patient or medical personnel of the potential problem.

Stabilization of VidaPen in Moving Patients

Being able to place the IO needle precisely in the target area of the tibia is a concern when patients are moving or have the potential to move. Drilling in the wrong place could subject the patient to harm. Special cases of such movement include patients suffering from status epilepticus, and violent patients (drug overdoses or mental status changes) that need to be controlled for their safety and treatment. Epileptic patients may shake violently for prolonged periods, which makes starting an IV nearly impossible. Likewise it may be difficult in these patients to accurately place the VidaPen for IO insertion. Although the target area for successful IO placement is much larger than the target for placement of an IV, this problem will be minimized with a stabilization device. The device must be easy to apply, even in difficult situations in the field.

Figure 55:
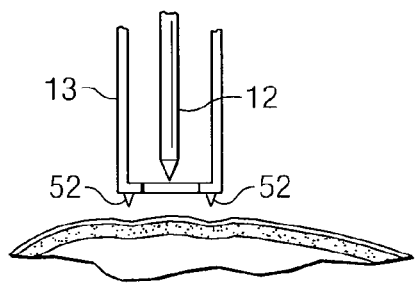
FIG. 55 depicts a mechanism for stabilizing an intraosseous device before insertion.

FIG. 55 depicts the shield 13 of the VidaPen as it is placed against the skin. Stabilization takes place by the placement of cleats 52 on the shield 13. Another version provides for adhesives to be applied to the shield.

Figure 56A:
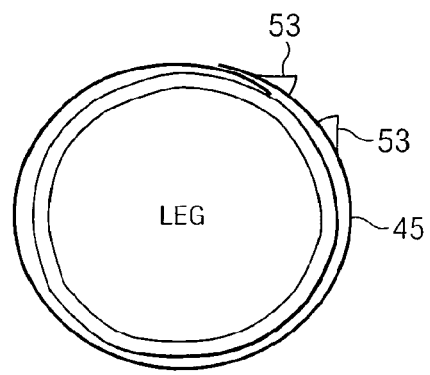
FIGS. 56A-58 depict a different mechanism for stabilizing an intraosseous device before insertion.
Figure 56B:

FIG. 56A shows a cross-sectional view of a strap 45 that is fitted with a plastic (or other suitable material) guide 53. The strap 45 may be a modified blood pressure cuff, an adhesive band or a Velcro strap that is placed around the leg. FIG. 56B shows a side view.

Figure 57:
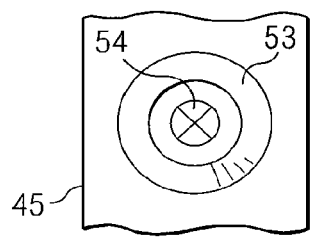

FIG. 57 illustrates that an "X" 54 is placed on the target area of the anterior tibia prior to attaching the stabilization guide 53. The access hole in the guide is placed over the target "X" 54 and the strap 45 applied around the leg.

Figure 58:
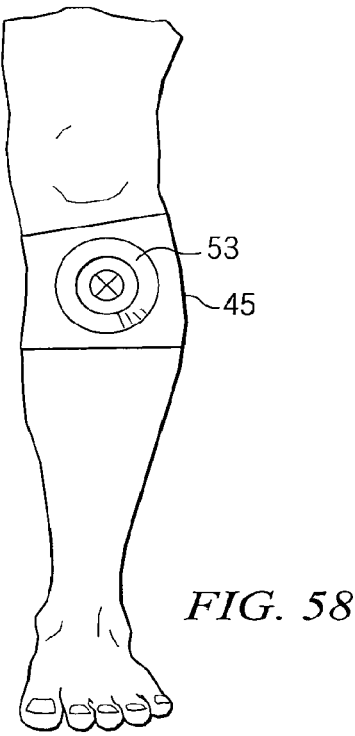

FIG. 58 shows the stabilization guide applied to the patient. The target "X" can be clearly seen within the guide 53 orifice.

Figure 59:
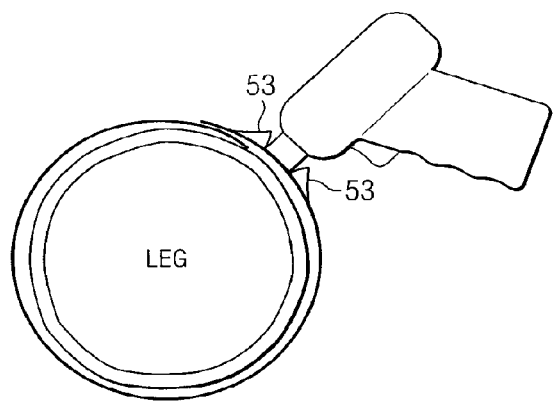
FIG. 59 depicts the operation of the mechanism of FIGS. 56A-58.

FIG. 59 shows the VidaPen being used in the patient equipped with the guide. The plastic guide forms a female cone that accurately fits the VidaPen. The VidaPen can be further stabilized with Velcro straps prior to drilling (inserting the IO needle).

VidaVac (Oncology Biopsy Needle)

Oncologists sometimes are not able to successfully obtain a suitable specimen because of mechanical problems. Biopsy needles used today often come out empty because they failed to capture a specimen of bone. When they are successful, the specimen obtained is often inconsistent. Significantly, two procedures are often required because one instrument is required to obtain the bone specimen (biopsy) and another instrument (resulting in a second procedure) is required to obtain the liquid marrow specimen. VidaVac addresses these problems with a powered biopsy needle combined with a specimen needle that can be performed in one procedure.

Figure 60:
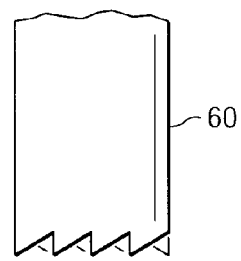
FIGS. 60 and 61 depict different biopsy needles.

FIG. 60 shows the tip of the biopsy needle 60, which is serrated for better cutting as it is introduced into the target bone. This tip is common on some biopsy needles in use today.

Figure 61:
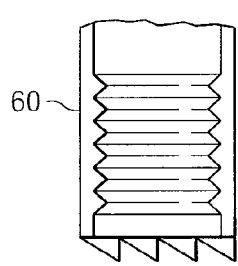

FIG. 61 shows a unique feature of an inner threaded biopsy needle that will help grab (purchase) the specimen during insertion of the needle. This is made possible by the powered rotation of VidaVac I.

Figure 62A:
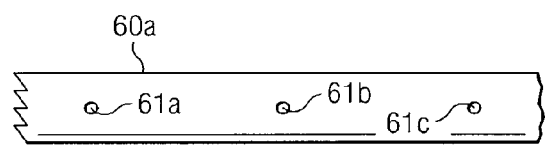
FIGS. 62A and 62B depict an inner and an outer biopsy needle.
Figure 62B:
Figure 62C:
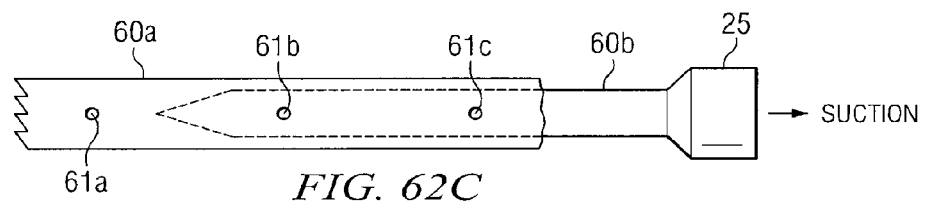
FIG. 62C depicts the operation of the needles of FIGS. 62A and 62B.

FIG. 62A shows three holes 61a, 61b, and 61c (ports) on the biopsy needle 60a. The purpose of 3 holes is to provide three sites for aspirating marrow specimens. Currently three separate procedures are required because only a few cc's can be obtained at any one site before systemic blood is retrieved instead of marrow. With the three-hole design, 3 separate sites can be accessed with one stick (procedure). This is accomplished by incorporating 3 holes in the outer needle 60a and having one hole 62 in the inner (sampling) needle 60b (FIG. 62B). Suction is applied to the inner needle 60b (trocar) and because it is first aligned with the distal hole, a sample from the distal hole is obtained. When sufficient sample is removed, the inner needle 60b is moved outward to align with the next orifice to aspirate the next specimen (FIG. 62C). When sufficient sample is removed from hole 61b the inner needle is withdrawn to the 3rd hole 61c where the final sample is taken.

Further, the needle may be coated with Heparin or other anticoagulant to prevent clotting.

FIG. 63 shows a method of controlling placement of the inner needle for various sampling sites. The biopsy needle 60a, with the sampling needle 60b inside is drilled into the target bone. The distal hole is aligned with the sampling needle orifice. Then a lever (or switch) is moved that aligns the sampling hole with the next orifice to obtain subsequent specimens.

FIG. 64A depicts a split needle design to insure a solid sample of bone with every biopsy attempt. A spilt needle 65 contained within the outer cutting needle 66 is drilled (inserted) into the bone to be biopsied. FIG. 64B shows that as the inner needle 65 is withdrawn from the outer cutting needle 66, knobs 65a and 66a along the corresponding walls cause the tips of the split needle to clamp together, thus capturing the specimen and breaking it loose from the surrounding tissue. FIG. 64C shows an end view from inside the outer needle 66. FIG. 64D show a cross-section of an inner needle 65.

VidaVac I (Powered Biopsy Device)

Currently, oncologists use a biopsy needle that is manually inserted, often with considerable force and difficulty. The procedure is painful for patients and time consuming for the doctor. Risks are high because of excessive handling of blood contaminated sharp instruments are required. Accidental needle sticks and missed targets further complicate the procedure. VidaVac solves these problems with a powered biopsy needle.

Figure 65:
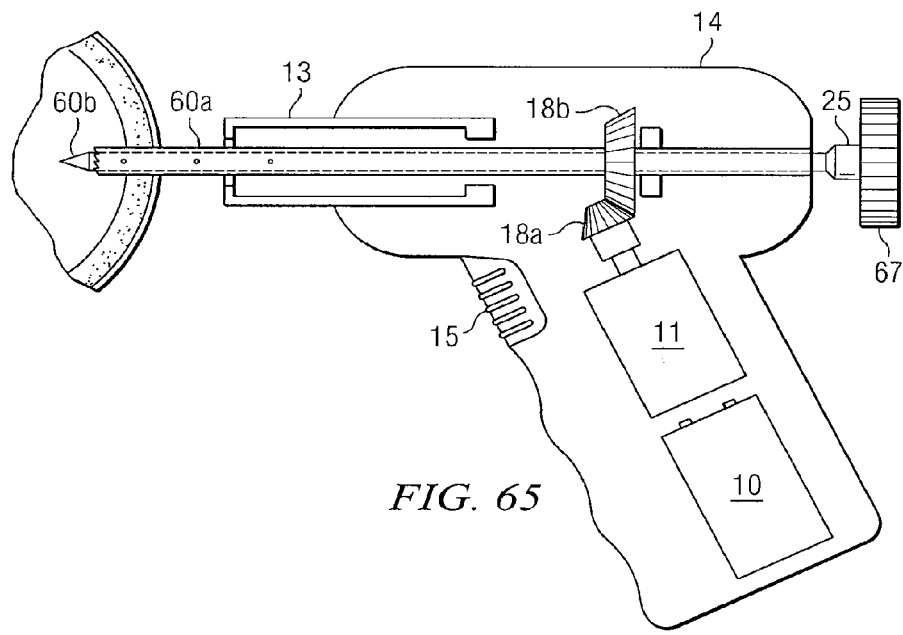
FIG. 65 depicts a biopsy device.

FIG. 65 depicts the principal features of the VidaVac powered biopsy device. It illustrates the combination biopsy needle and sampling needle inserted into the target bone (iliac crest). The key to its use is a gear 18b that is attached to the needle shaft. This allows the Luer lock end of the needle to be accessed in the usual fashion. This is necessary to remove specimens and place trocars and biopsy needles into the outer drilling needle. A handle 67 is attached to the inner needle that allows manual manipulation as the oncologist sees fit. Suction can be applied to the outer needle or the inner sampling needle. A high torque motor is used with a DC battery. The entire device can be disposable or the driver can be reusable, depending on the application.

Figure 66:
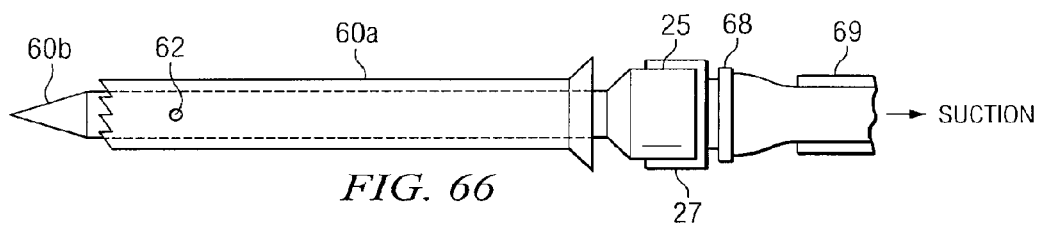
FIG. 66 depicts a method of applying suction to a rotating needle.

FIG. 66 illustrates a new (novel) method of applying suction to the rotating needle. This is especially important in VidaVac II, used for bone marrow transplants which require multiple sites (up to 20 per patient) in order to obtain enough marrow (sample size) to perform a routine bone marrow transplant. Currently this is a labor-intensive procedure. The needle is manually inserted under considerable force. This force often causes loss of control or operator fatigue. When the needle is in place, the trocar is removed and a syringe is attached to aspirate a few cc's of the marrow specimen. Then the needle is withdrawn. A new site is penetrated a centimeter from the first site and the procedure repeated. With this new design, several of these steps are eliminated. First the powered biopsy needle is easily inserted under precise control. Secondly this embodiment shows a swivel connector that allows the suction to remain connected during the drilling procedure. The seal is made of Teflon or silicone rubber and is connected to the Luer lock end of the needle. The reason this is important is to permit the oncologist to move the biopsy needle from site to site without having to remove the syringe and reconnect it. Suction is applied by a foot-switch and the specimen is collected in a jar near the needle. This will save time, increase safety, insure sterility, and decrease the hassle factor involved in these procedures.

Special Considerations for Cancer

Extravasation (leakage) of cytotoxic drugs into the subcutaneous tissues during cancer treatment can be devastating.

To prevent extravasation (leakage) of cytotoxic drugs using the VidaPen I, special precautions must be taken.

Use of a treaded needle, which has been shown to decrease leakage

Use of a tapered needle with progressively larger diameter to make a tighter seal Use of methylmethacrolate or other sealant to provide a tight seal.

The injection of methylene blue dye into the needle prior to use to detect any leak.

Figure 67:
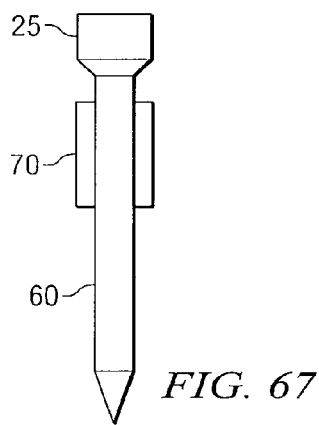
FIG. 67 depicts a different needle.

FIG. 67 shows the VidaPen I needle for chemotherapy coated with silicone or methylmethacrolate to provide a secure seal 70 to prevent extravasation.

VidaProbe VidaVent (for Neurosurgery)

Neurosurgeons frequently insert vents into the cranium after massive closed head injuries to monitor intracranial pressure. Preventing excessive pressure can make a profound difference in the outcome of a brain-injured patient. Currently, the placement of such a device takes several steps and considerable time. VidaVent is designed to automate the procedure by providing a power drill to drive in the probe in one short step. The results will be a faster, safer and more palatable procedure.

Figure 68:
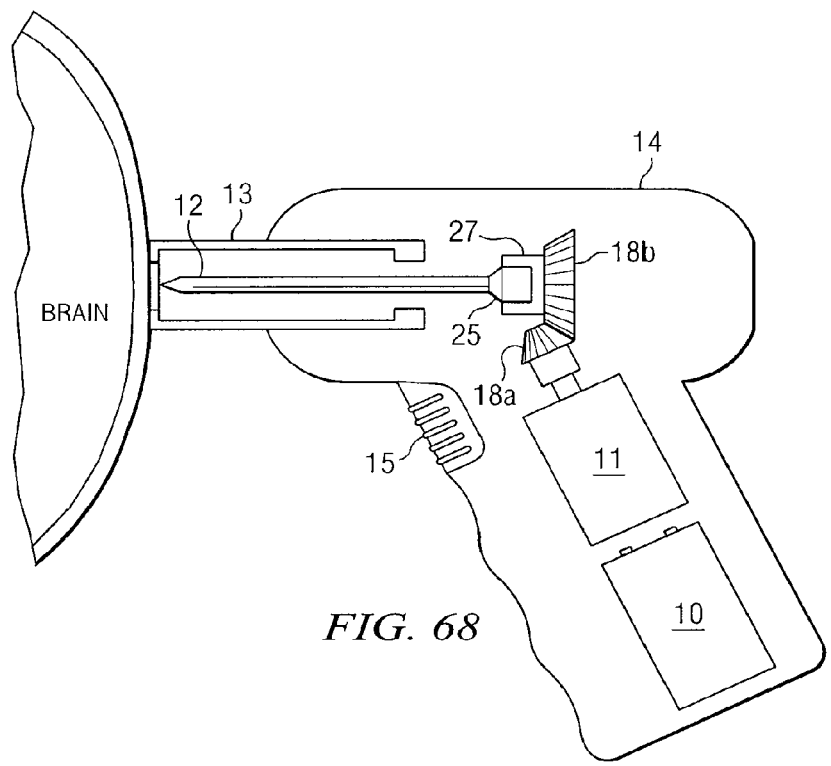
FIG. 68 depicts an intracranial device.

FIG. 68 portrays the VidaProbe placed on the head of a brain-injured patient. The configuration and motor/battery is similar to VidaPen I. The needle in this case is specialized to perform as a vent and/or a pressure detector.

Figure 69:
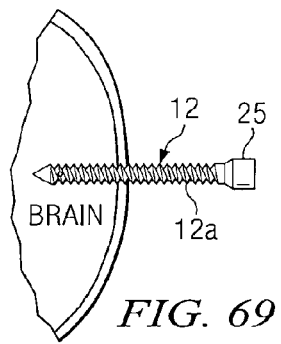
FIG. 69 depicts a different needle.

FIG. 69 depicts a screwed needle to control the depth of penetration into the brain.

Figure 70:
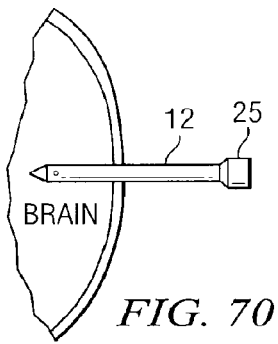
FIG. 70 depicts a probe.

FIG. 70 shows a standard probe that was automatically inserted into the brain and sealed.

Figure 71:
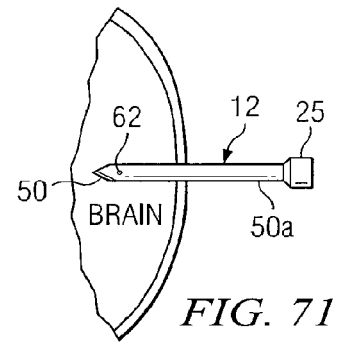
FIG. 71 depicts a different needle.

FIG. 71 details the VidaProbe needle. It may be hollow to permit injection of fluids or drugs i.e. antibiotics, or to withdraw excessive fluid or blood, or to sample cerebral spinal fluid for analysis. The tip of the needle contains the pressure transducer to measure pressure. The electrical wire from the transducer may exit the needle separate from the Luer lock port. The connector may be a standard Luer lock or any other conventional connector to allow monitoring of pressure directly from the fluid. Either of these models may be attached to a monitor or a computer to alert medical personnel of impending problems. Software may also be used as a servomechanism to automatically control pressure or other parameters.

The probe may detect pressure, chemicals, temperature, $O_2$ stats, $CO_2$ levels, or lactic acid.

The connector may be mechanical or electrical.

VidaPed (Pediatric Version)

Currently, infants and young children are candidates for standard manually inserted IO needles. Yet, some reluctance on the part of medics and doctors remains because the manual insertion process takes time and skill. In the process, the needle grinding through the bone causes concern to the provider. In addition, when the hard cortex is breached (entered) the needle may penetrate the opposite cortex (which causes extravasation) because of the large manual pressure being exerted. Therefore, the VidaPen is designed to permit use in small infants in a kinder/gentler way. Minimal pressure is required, because of the powered drill and so precise control of the depth of penetration can be maintained. The entire procedure is one-step and automatic, making it easier for the medic and the patient.

Figures 72, 73A, 73B, 74, 75:
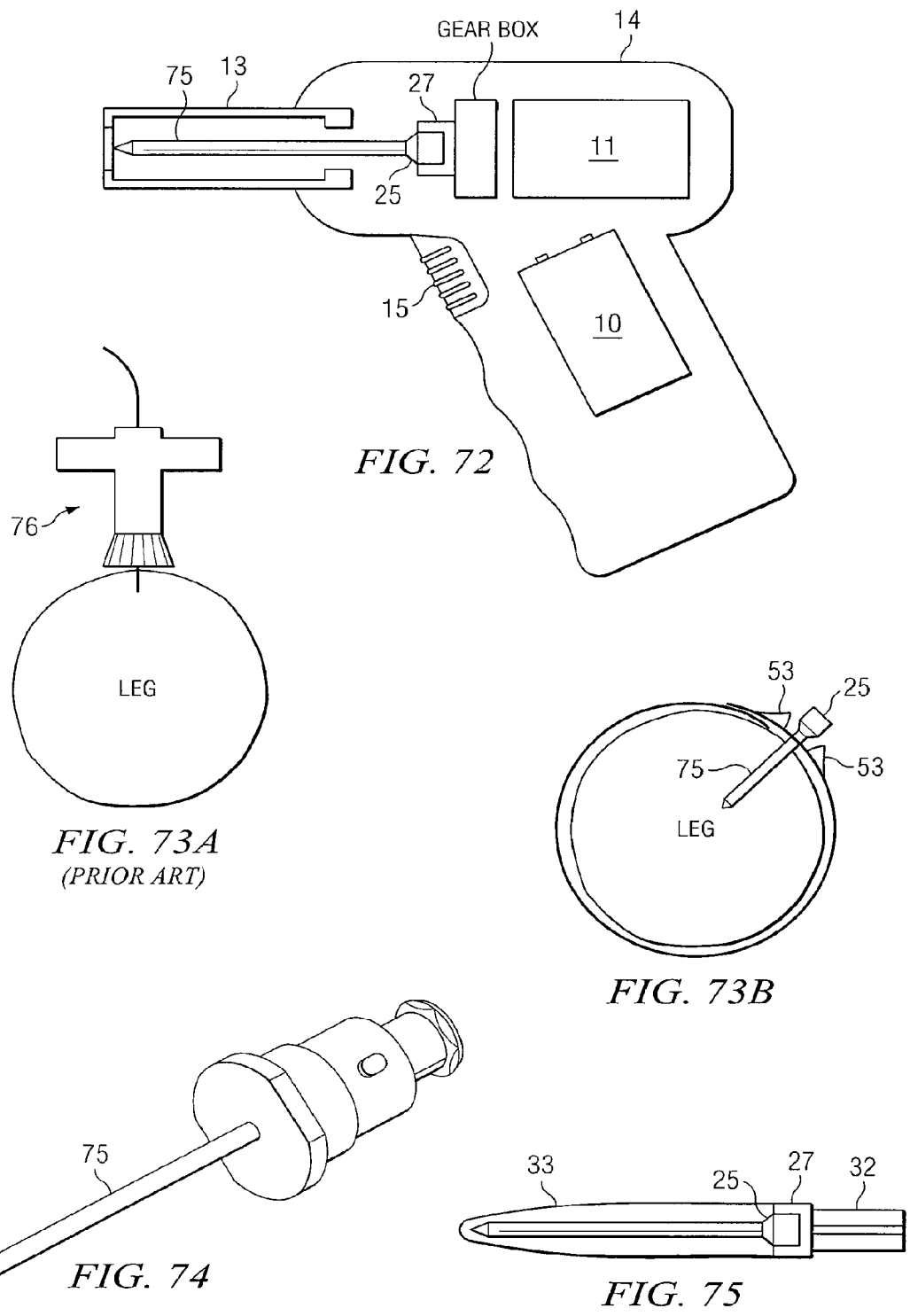
FIG. 72 depicts a different intraosseous device.
FIG. 73A depicts a needle inserted into a patient.
FIG. 73B depicts a different needle inserted into a patient.
FIG. 74 depicts a different intraosseous device.
FIG. 75 depicts a different needle.

FIG. 72 depicts the small pediatric VidaPen. It is much smaller than the adult model, is lightweight, and quiet. It has a smaller needle 75, which is required for pediatric applications. Otherwise it is similar to the adult version.

FIG. 73A shows the current pediatric IO needle mounted on the leg. Note the high profile that is difficult to secure. It leads to instability because of its height. The long design of the Jamshidi needle 76 is necessary for the medic to manually insert the needle. During transport of the patient, extraordinary measures must be taken i.e. tape and gauze, to keep the needle from breaking off or coming out of the leg. This rocking of the needle also causes loosening, that may increase extravasation.

FIG. 73B shows the VidaPed IO needle, which is short and stable. It can be designed to be short and safe (will not penetrate the opposite cortex of the bone) because the power driver does not require the long handle to function.

FIG. 74 also shows a pediatric configuration.

VidaVet (for Veterinary Applications)

Veterinarians frequently need to access the vascular system of companion animals for the purpose of diagnostics and treatment. These small animals often have tiny veins that are very difficult to access. While there is great need for this device in the veterinary market, vets require devices that are cheap and reusable. Therefore, the VidaVet will consist of a reusable driver and sterile disposable (throw away) needles.

FIG. 75 shows the IO needle for the VidaVet. It is kept sterile by a seal between the female Luer lock and the chuck. Another seal (standard needle shield) protects the needle until the Vet is ready to use the device. The VidaVet will be small, like the VidaPed.

After implantation of the IO needle, a special cap or cover will be strapped on to protect the device from self-destruction by the animal (prevent the animal from inadvertently pulling out the needle.

Spring Powered VidaPen I—Reusable

It may be advantageous to be able to rewind the spring for additional IO attempts should the first attempt fail. The ability to reload or rewind the spring is also necessary for applications using a reusable handle (with disposable needles). In these cases it is necessary to provide an easy mechanism to accomplish the rewind.

FIG. 76 shows a wind up knob 77 on the back of the driver, which makes it easy for the user to rewind by using a twisting action. This could be linked directly to the spring or use a gearbox for further mechanical advantage.

FIG. 77 shows an embodiment of a one-way ratchet to accomplish the wind up action.

Figure 78C:
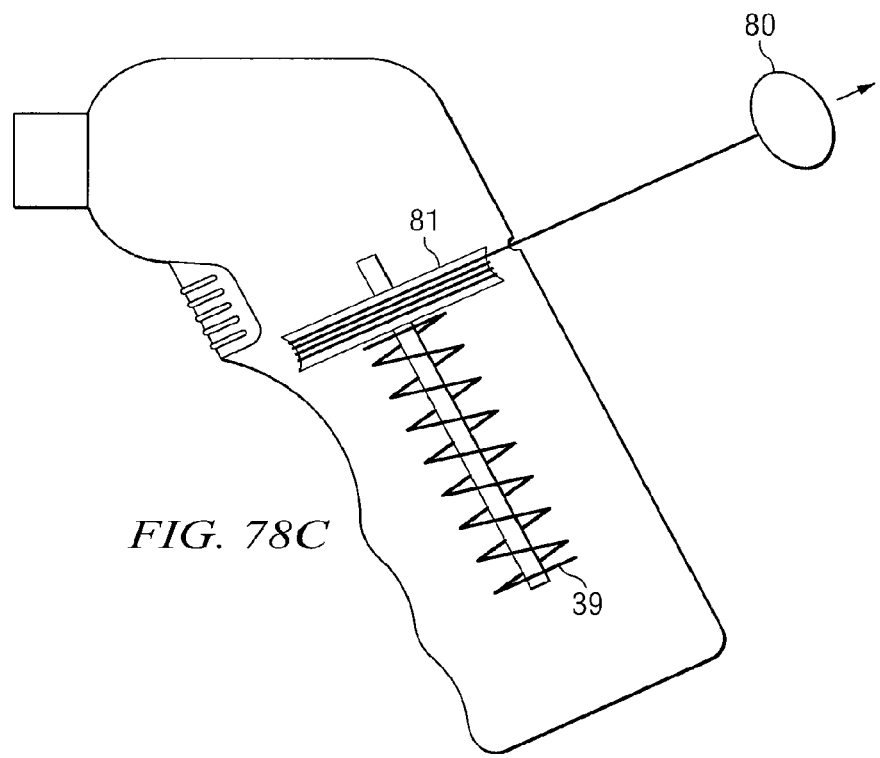

FIGS. 78A, 78B, and 78C show several configurations of a pull string (or cable) that are attached to a spool 81. By pulling on the handle 80 (knob) attached to the cable the spring is re-wound.

Figure 79A:
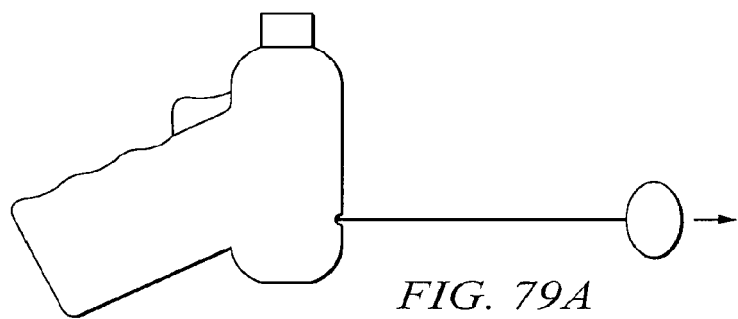
Figure 79B:
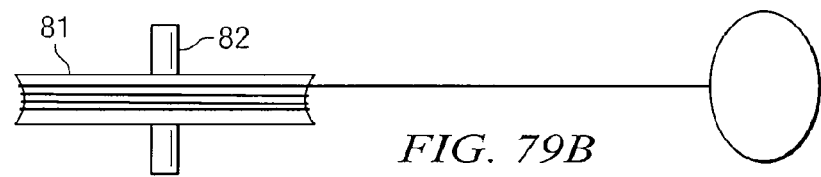

FIGS. 79A and 79B show the string attached to the spring shaft 82 by a spool 81 that collects the string and is itself spring loaded to allow repeated pulls, much like a hand-starting lawnmower motor. The spool may be connected directly to the spring 39 or connected to a gearbox or transducer before attaching to the spring.

Figure 80A:
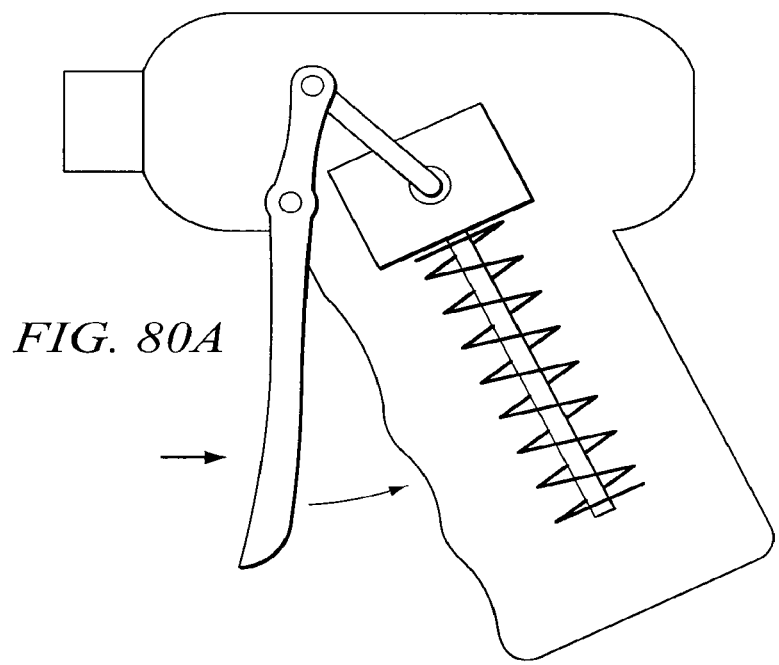

FIG. 80A shows a handle grip to rewind the spring. Compressing the grip and squeezing it toward the handle of the driver transmits power to rewind the spring via a gearbox or lever arrangement. Two configurations are shown to illustrate practical applications.

Figure 80B:
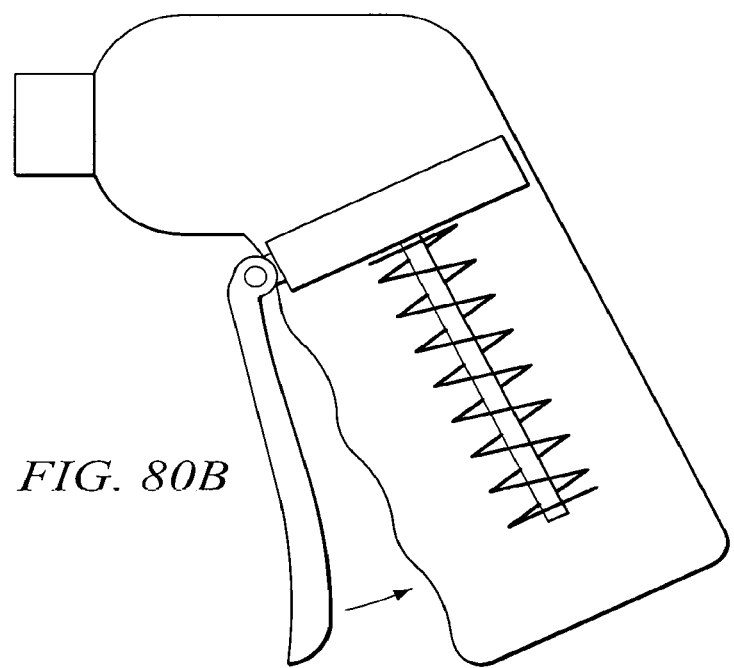

FIG. 80B shows a hinged grip that is squeezed by the user to provide power to rewind the spring. Several mechanisms can be used to transfer the to-and-fro motion of the grip to rotational power to spin the needle. These are gear arrangements and/or lever/ratchet configurations.

Spring Powered—Speed Control

The spring can be made with enough strength to give adequate torque to the needle for drilling through most bone applications. However, the rotational speed provided by the spring may be excessive and therefore, a means of controlling that speed is required.

FIG. 81 illustrates placing a governor 83 on the rotational end of the spring. This governor will allow the rotation to meet the optimum rotational speed for any application.

FIG. 82 shows the inside of a governor, which uses a viscous fluid to provide speed control. A fan 84 (turbine) inside the fluid chamber 85 is attached to the spring. Speed can be designed (determined) by using a higher viscosity fluid (providing maximum slowing), while a lower viscosity fluid provides less slowing. Air or gas (instead of a fluid) could provide minimal slowing of rotational speed.

FIG. 83A shows the use of rotating weights to provide rotational speed control. These weights 86 (shoes) rotate with the shaft of the spring's power train and slide against the housing 87 (the race). The faster the rotation, the more centrifugal force that is applied. Fairly precise speeds can thus be maintained by designing the proper weight and rotational arm of the shoes. Heavier weights (FIG. 83B) will provide maximum slowing while lighter weights will provide minimal speed control.

Hand-Powered VidaPen I

It may be desirable to dispense with motors and springs altogether and power the rotation of the needle by hand. This would eliminate several potential problems associated with stored power devices and make the function totally dependent on the user.

A hinged grip that is squeezed by the user may be used to provide power to rotate the needle. Several mechanisms can be used to transfer the to-and-fro motion of the grip to rotational power to spin the needle. These are gear arrangements and/or lever/ratchet configurations.

A push handle may be used to propel a rod into the driver. This rod is fitted with spiral groves along the shank that mates with knobs in the gearbox to provide rotational power. This is mechanism is similar to Yankee screwdrivers. Two hands would be required—one to push the handle and the other to stabilize the driver.

An inertia motor may be used to drive the needle. This can be a flywheel or other spinning weight that will be used to rotate the needle. The user will provide rotation to the flywheel just prior to use by using any one of the mechanisms illustrated in FIGS. 76, 77, 78, 80, and in this section.

Ergonomic Configurations

A key to successful use of the VidaPen is to configure the design to allow a natural interface between the user and the device as it is applied to the patient. Consideration is made for a grip that allows the medic to control the device and hold it securely in a natural position. In addition, the device must "feel" like other common tools used by the medic and allow steady positioning during use. Coupled with this, the user must be able to see the target area and not have to assume an unnatural position to do so. Therefore, his/her eyes must be able to see the target area easily and in proper alignment throughout the procedure.

FIG. 84 shows a design that allows all the forgoing parameters in a comfortable and secure interface between the device and the user. Note the natural position of the hand and the eyes for proper alignment and control.

Mechanism to Allow Ergonomic Design

While ergonomics are important in the design of VidaPen, proper function is essential. In order to embody the mechanism in such a well-designed driver (handle) certain aspects of power transfer must be considered.

Figure 85:
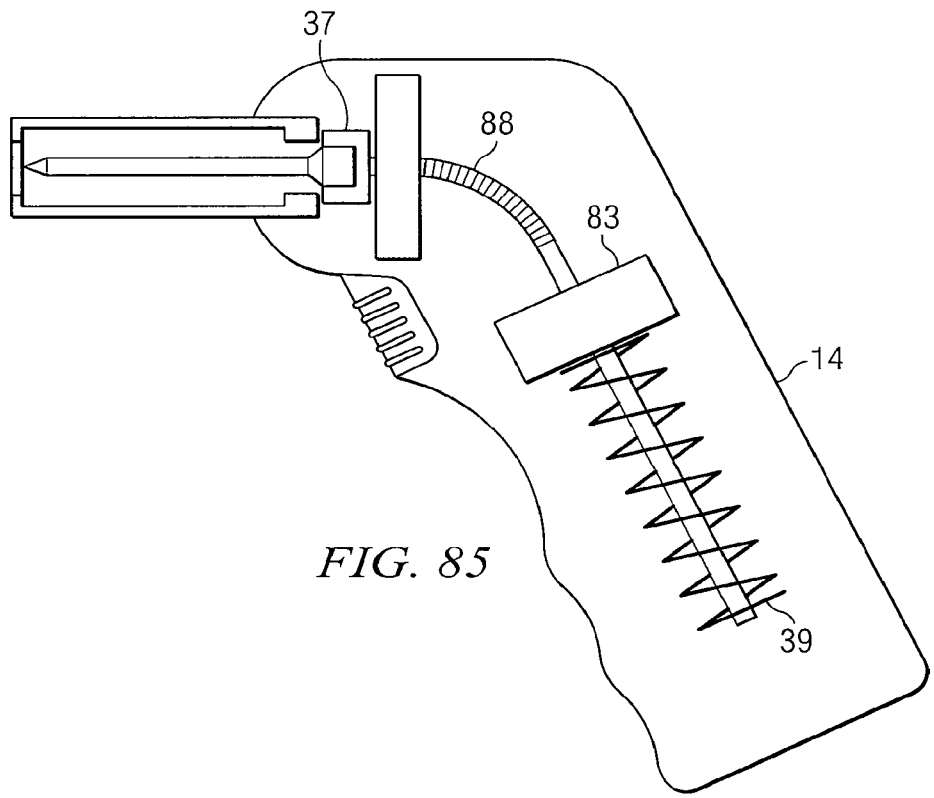
FIGS. 85 and 86 depict different mechanisms for transferring power.

FIG. 85 shows power from a spring or a motor/battery drive being transferred to the needle chuck 37 via a flexible shaft 88.

Figure 86:
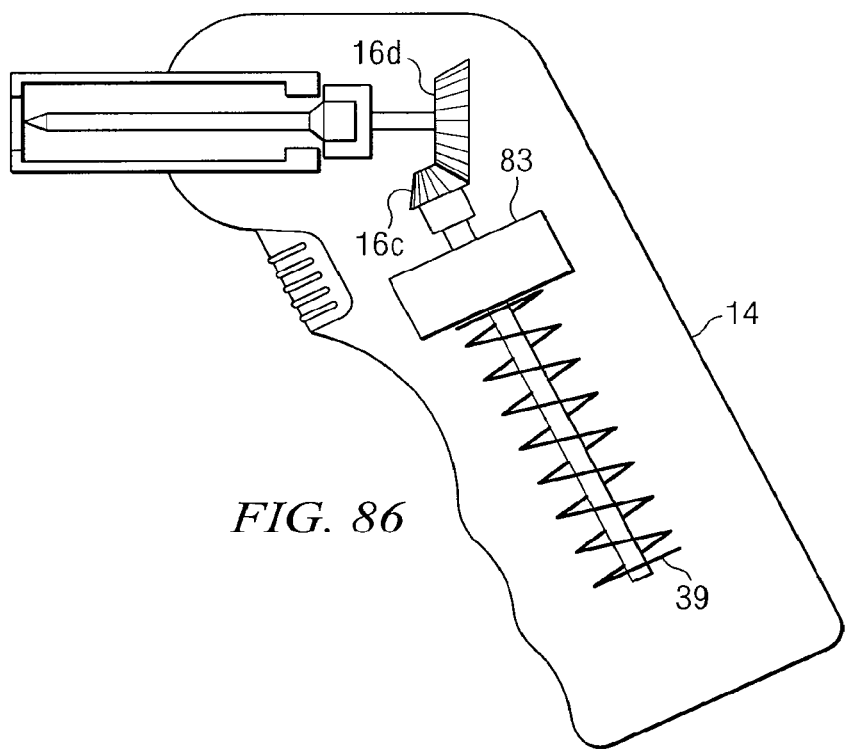

FIG. 86 shows the same configuration using an inside (45 degree) gear arrangement. A motor or a spring can power both of these designs.

Figure 87:
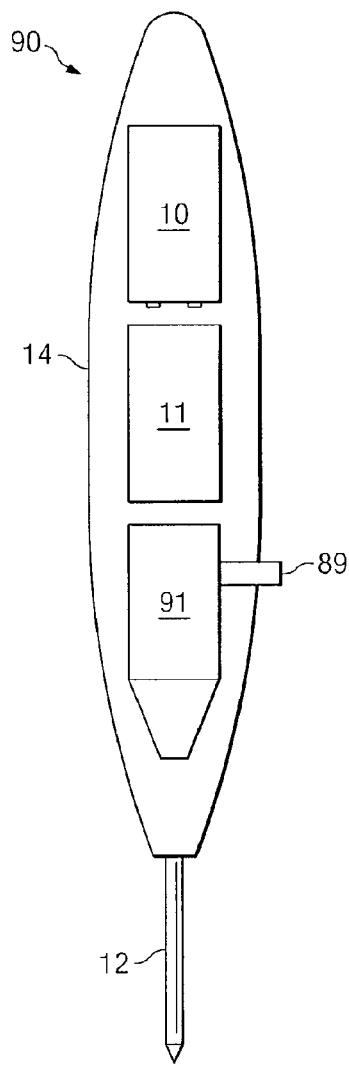
FIG. 87 depicts a different intraosseous device.

FIG. 87 also illustrates an optional connector port 89 that can be accessed in order to connect device 90 to an external source of drugs or fluids. The distal end of device 90 may incorporate a male connector that connects to a female connector of a hub formed on needle 12. Alternatively, needle 12 may be rotatably connected to housing 14 by a quick-release mechanism.

In some embodiments device 90 may be equipped with an on/off switch for starting and stopping the power supply. A battery recharger may be included in some models.

In some embodiments device 90 may include a plunger mechanism (not expressly shown) that is attached to the proximal end and designed to engage the interior surface of reservoir 91.

Figure 88:
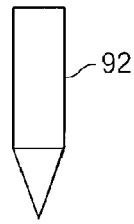
FIG. 88 depicts a drug chamber.

FIG. 88 illustrates a drug chamber 92 that can be substituted in the device for fluid reservoir 91. In one embodiment of this invention drug chamber 92 may be quickly interchanged with fluid reservoir 91 using a quick-release spring loaded mechanism (not expressly shown).

Figure 89:
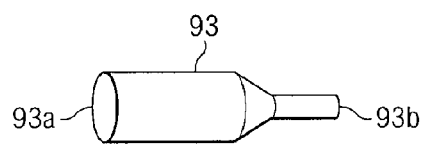
FIG. 89 depicts a connector.

FIG. 89 illustrates optional connector 93 that may be attached at one end 93a to connector port 89 of device 90. The other end 93b of the connector is configured to attach to a standard intravenous (IV) tubing.

FIG. 90 illustrates device 90 after needle 12 has been inserted into the tibia of a patient's leg. Connector 93 may be attached to connector port 89 of device 90 at one end 93a and to IV tubing 94 at the other end 93b so that the patient may receive IV fluids from a sterile bag 95.

APPENDIX I

Special Uses of the VidaPen

Broad Application:

VidaPen technology has great promise for almost any serious emergency that requires intravenous (IV) access to administer life-saving drugs or fluids, when traditional IV access is difficult or impossible. These life-threatening conditions include, but are not limited to:

NOTE: IO is to be used primarily as a "bridge" (temporary fluid and drug therapy) until conventional IV sites can be found and utilized. This occurs because IO fluids stabilize the patient and expand their vascular compartment.

Emergency Medicine Indications (VidaPen):
  Anaphylaxis (epinephrine, steroids, antihistamines, fluids, and life support)
  Arrhythmia (anti-arrhythmics, electrolyte balance, life support);
  Burns (fluid replacement, antibiotics, morphine for pain control);
  Cardiac arrest (epinephrine, atropine, amiodarone, calcium, xylocaine, magnesium);
  Congestive heart failure (life support, diuretics, morphine, nitroglycerin);
  Dehydration (emergency port for life support, antibiotics, blood, electrolytes);
  Diabetic Ketoacidosis (life support, electrolyte control, fluid replacement);
  Dialysis (emergency port for life support, antibiotics, blood, electrolytes);

Drug overdose (naloxone, life support, electrolyte correction);
Emphysema (life support, beta adrenergics, steroids);
Hemophiliacs (life support, blood, fibrin products, analgesics);
Osteomyelitis (antibiotics directly into the site of infection, analgesics);
Pediatric applications (shock, dehydration, nutrition, electrolyte correction);
Seizures (anti-seizure medications, life support, fluid balance);
Shock (life support fluids, pressor agents, antibiotics, steroids);
Sickle cell crisis (fluid, morphine for pain, blood, antibiotics);
Trauma (emergency port for life support fluids, antibiotics, blood, electrolytes);
Stocking of Emergency Equipment:

After acceptance in the emergency medical community as a reliable alternative for accessing the vascular system, VidaPen could become the standard of care for administering medications in life-threatening situations when IV access is difficult. Appropriately priced, the VidaPen could become required equipment for basic emergency kits:

Ambulances:

More than 35,000 Advanced Cardiac Life Support (ACLS) ambulances are in service in the U.S. Each is equipped with emergency drugs and devices. Most are required to carry intraosseous needles and paramedics are trained in their use for pediatric emergencies. Paramedics often experience great difficulty establishing IV access in life threatening emergencies such as drug overdoses, cardiac arrest and status epilepticus. Since they are the first on the scene in most serious emergencies, they would welcome a device like the VidaPen, which could help them rapidly, administer medications and treat the emergency before permanent damage to the patient occurs. There is nothing like VidaPen on the market and some patients desperately need this route for emergency drugs;

Emergency Rooms:

More than 4,000 emergency rooms in the U.S. are required to treat life-threatening emergencies like shock trauma and cardiac arrest. ERs are stocked with the latest devices and equipment to help patients receive state-of-the-art treatment. However, there is no more exasperating situation for the physician or potentially catastrophic condition for the critical patient, than the inability to establish intravenous access. VidaPen can provide a simple and straightforward solution for an extremely difficult clinical problem;

Hospital Crash Carts:

Hospitals are required to provide crash carts on every patient ward. It is estimated that 6,000 U.S. hospitals stock more than 60,000 crash carts. These crash carts are stocked with defibrillator, IV access devices, including central venous catheters, IV fluids and drugs for common emergencies. Nurses and other healthcare workers using these crash carts are often inexperienced in such emergencies and have difficulty establishing IV access. VidaPen can provide the long sought IV alternative in the difficult patient;

Military:

Automatic injectors are widely used in the military. During Desert Storm, combat soldiers carried an atropine auto-injector for nerve gas poisoning. Current auto-injectors are limited to intramuscular injections. The VidaPen could vastly expand the scope of treatment to include intravenous drugs, without having to be skilled in the technique of intravenous insertion.

Internal Medicine/Critical Care:

Most acute care hospitals in the U.S. operate Intensive Care Units (ICUs) for seriously ill patients. Establishing and maintaining venous access in these patients is often a challenge. VidaPen would be a welcome device for administration of drugs and fluids for these critical patients.

Cancer Applications (VidaVac):

In addition to the emergency medicine applications, where injection is the mode of operation, this technology can also be used to aspirate fluid. Thus, the VidaVac is ideally suited for the treatment and diagnosis of cancer.

Bone Marrow Harvest

For bone marrow transplants in cancer

Bone Marrow Diagnostics

For diagnosing cancer and hematological diseases

Infusion of Chemotherapy and Fluids

For cancer treatment, when IV access is difficult or veins have been destroyed by chemotherapy.

Secondary Applications:

VidaPen has great promise for many other diseases. Secondary applications will be developed after success of the primary applications. Some may evolve into primary markets. These include:

Neurosurgery (VidaVent);

Cranial vent (closed head injury requiring monitoring of intracranial pressure)

Stem Cell Harvest;

For regeneration of damaged tissue (heart muscle, articular surface, nerves and spinal cord, bone and spinal fusions)

Veterinary Market.

Intraosseous access has been used extensively in animal research. Increasing use of parenteral medications in companion animals accompanied by difficulty finding suitable veins to administer these drugs makes IO infusion an attractive alternative. The VidaVet appears ideally suited for these applications.

Epilepsy, An Example of VidaPen's Unique Solution:

Ten percent of the population experience a major seizure in their lifetime and more than 2,500,000 people in the United States have epilepsy. Grand mal seizures represent one of the most dramatic events in medicine. During the seizure, which usually lasts 60 to 90 seconds, patients typically fall to the ground, become rigid with trunk and extremities extended, and shake violently. The most dreaded progression of seizures is status epilepticus, a condition defined as a continuous seizure lasting more than 30 minutes or two or more seizures that occur without full conscious recovery between attacks. Convulsive status epilepticus requires urgent, immediate treatment. Patients are at risk for serious injury, hypoxemia, circulatory collapse, permanent brain damage and death. The overall mortality of convulsive status epilepticus is up to 35 percent.

Intravenous Access Required:

Intravenous access with a large bore needle/catheter must be established to administer anticonvulsant medications. These include a benzodiazepine followed by phenytoin and/or phenobarbital for immediate seizure control and prevention of further seizures. There are no satisfactory oral, rectal, or intramuscular medications that will control status epilepticus.

Clinical Need:

The problem facing clinicians and paramedics treating patients with status epilepticus is the difficulty establishing venous access. Without adequate venous lines none of the effective anticonvulsants can be given. During seizures the violent shaking makes accessing a satisfactory vein difficult.

Often after the line is established, further shaking dislodges the IV or causes it to infiltrate.

Danger of Accidental Puncture:

Further, caregivers are at great risk of puncturing themselves with a needle when attempting to establish venous access in a patient during a seizure. Through no fault of their own, seizing patients, by jerking and thrashing around, turn the safest procedure into a terrifying venture. Doctors, nurses, and paramedics work in mortal fear of contracting AIDS and hepatitis through an inadvertent puncture with a contaminated needle.

Central Venous Access:

In an attempt to solve the venous access problem, emergency physicians and intensivists have turned to establishing a central line (intravenous catheter placed in a large central vein such as the subclavian or femoral vein). However, with this method, even under ideal conditions, there is an increased incidence of serious side effects such as pneumothorax, hemothorax, inadvertent puncture of a major artery, infection, venous thrombosis, and embolus. In the case of a patient with status epilepticus, this method becomes increasingly difficult and dangerous for all of the above-mentioned reasons. Therefore, most doctors are reluctant to even attempt a central line until seizures have ceased.

VidaPen provides alternative, safe IV access:

The VidaPen has been designed to quickly, and safely access the vascular system in difficult cases, like status epilepticus, giving medics the opportunity to administer crucial medications (see the Scientific Appendix for a more complete description of VidaPen's use in epilepsy).

Other Emergency Conditions that Will Benefit from the VidaPen:

Dialysis patients who often come to the emergency room in life threatening situations such as pulmonary edema (water on the lungs) or high potassium leading to cardiac arrest. These patients typically have troublesome or non-existent veins. The VidaPen could give these patients hope for a better quality of live and decrease their mortality.

Suicide attempts and drug overdoses often present in coma requiring immediate intravenous access to give antidotes and life saving medications such as Narcan. These patients usually have difficult venous access due to long term abuse of their veins. The VidaPen can give these patients an alternate access route while improving the safety of the healthcare workers.

Trauma victims often present in shock due to blood loss requiring swift replacement to save vital organs. Because of the shock condition (decreased blood pressure), veins collapse and are often impossible to find. The VidaPen can save precious minutes for paramedics and trauma surgeons responsible for their care.

Cardiac arrest, drug overdoses, diabetic ketoacidosis, arrhythmias, burns, stroke, coma, etc. VidaPen provides a logical, safe and easy alternative to IV access in all such serious emergencies.

APPENDIX II

Emergency Medicine, "My Kingdom for an Intravenous Line"

Life-threatening medical emergencies affect millions annually. Standard treatment requires administering intravenous (IV) drugs and fluids. Yet, for more than 4 million patients annually this treatment is not available because intravenous lines cannot be readily established. For these patients, finding a suitable alternative treatment becomes a monumental and sometimes impossible task. Thousands of patients with such emergencies die because life saving medications cannot be administered.

An accepted alternative route to give IV medications is through the bone marrow (intraosseous, or IO, access). All drugs tested enter the circulation just as rapidly via the intraosseous route as they do when given intravenously. In fact, the bone marrow is considered a large non-collapsible vein. Currently, the IO route is used for alternative emergency access in pediatric patients, whose bones are soft enough to permit manual insertion of IO needles. However, no practical device is available for IO access in adults, because of their hard bones.

VidaPen I & II, New Capability for Emergency Medicine:

VidaPen is being developed to meet this clinical need. The VidaPen I is a small battery powered device that penetrates the bone with a hollow drill that provides IO access. VidaPen II is a small auto-injector that penetrates the bone with a hollow drill and automatically injects medications into the circulation in less than 3 seconds. VidaPen's approach vastly expands the usefulness of IO administration in the pediatric population and also, for the first time, makes possible the use of IO technology for the adult population.

VidaPen technology offers great promise for almost every serious emergency that requires rapid and reliable vascular access to administer life-saving drugs or fluids, when traditional IV access is difficult or impossible. Such emergencies include shock, trauma, cardiac arrest, drug overdoses, diabetic coma, burns, dehydration, seizures, allergic reactions, and arrhythmias. There are 100 million visits to emergency rooms annually. Statistics show that vascular access is difficult or impossible in 4 million patients annually.

Cancer, "Sometimes the Treatment is Worse than the Disease":

Cancer patients often endure pain and discomfort in their quest for a cure. Among the most painful procedures these patients must encounter is bone marrow aspiration (biopsy). This arduous procedure is necessary to make the correct diagnosis, to monitor the success of treatment, or to undergo bone marrow harvesting prior to transplantation. More than 30,000 bone marrow transplants are performed in the US annually and over 200,000 bone marrow biopsies are performed. Bone marrow sampling is not a gentle procedure and is difficult for both the patient and the physician. The instrument used to penetrate the bone is a large nail-like device. Oncologists push with considerable force and twist on the handle to grind through the harder crest of the bone, into the softer marrow, Safety (contracting AIDS) is a major concern for oncologists, because repeated manipulation of a blood-contaminated needle is necessary.

VidaVac I & II, New Instruments in the Treatment of Cancer:

Instead of having to push and grind into the bone, VidaVac I is a small battery powered instrument that permits the oncologist to automatically drill into the marrow with minimal effort to withdraw specimens for diagnostics (biopsy). VidaVac II automatically withdraws marrow for transplantation. The end result is a safe, successful completion of bone marrow harvesting with less pain for the patient. It enables oncologists to treat patients in a kinder, gentler way, significantly decreasing risks for the doctor and time for the procedure. VidaVac is ideally suited for the treatment and diagnosis of cancer in the following situations:

Bone marrow harvest: For bone marrow transplants in cancer.

Bone marrow biopsy: For diagnosing cancer and hematological diseases.

Infusion of chemotherapy: For cancer treatment, when IV access is difficult.

Other Applications:

Stem cell harvest (VidaVac): Stem cells taken from the bone marrow are targeted for regeneration of damaged heart muscle, nerves, spinal cord, cartilage, and bone;

Neurosurgery (VidaProbe): Closed head injury requiring introduction of a probe for monitoring and controlling intracranial pressure;

Veterinary (VidaVet): Venous access is difficult but necessary in many companion animals.

Emergency venous access is essential for the treatment of many serious diseases and conditions. Yet, many patients experience extreme difficulty obtaining timely emergency treatment because of the inability to obtain or maintain venous access. VidaPen offers an alternative access route that can mean the difference between life and death. Currently there is nothing like VidaPen on the market and some patients desperately need this route for emergency drugs. Physicians and paramedics should readily adopt the VidaPen technology, because they universally embrace intraosseous (IO) access for emergencies in infants. The next logical step is to use the VidaPen for IO access in adults. Based on the clear need for an acceptable alternative method to deliver life saving medications when IV access is unavailable, the VidaPen should gain rapid acceptance, significantly penetrating this market. VidaVac affords oncologists a much-needed powered instrument for the diagnosis and treatment of cancer. Accessing the bone marrow is an essential, everyday procedure, which currently takes considerable effort. Oncologists should readily adopt this technology because of the simplicity and safety it offers their patients.

What is claimed is:

1. An apparatus for penetrating a bone and associated bone marrow comprising:
   a housing;
   a drill shaft rotatably disposed within the housing;
   the drill shaft operable to connect the needle assembly to a reduction gear assembly disposed within the housing;
   a reduction gear assembly disposed in the housing and coupled to the drill shaft;
   a motor disposed within the housing and coupled to the reduction gear assembly;
   a battery power supply and associated circuitry disposed within the housing and configured to power the motor;
   an intraosseous (IO) needle assembly configured to penetrate the bone and associated bone marrow, the IO needle assembly comprising:
      an outer needle having a first end, a second end with a plurality of cutting surfaces, and a lumen extending from the first end to the second end;
      a first Luer connector disposed on the first end of the outer needle in fluid communication with the lumen;
      an inner trocar having a first end and a second end with a plurality of cutting surfaces;
      where the inner trocar is disposed partially within the lumen and secured relative to the outer needle such that each of the plurality of cutting surfaces of the inner trocar are co-planar with one of the plurality of cutting surfaces of the outer needle;
   where the outer needle is configured to be coupled to the drive shaft via a second Luer connector to which the first Luer connector is connected.

2. The apparatus of claim 1, where the trocar is engaged with the second Luer connector.

3. The apparatus of claim 1, where the second Luer connector is releasably coupled to the drive shaft.

4. The apparatus of claim 3, where the trocar is engaged with the second Luer connector.

5. The apparatus of claim 1, where the first Luer connector is a male Luer connector.

6. The apparatus of claim 5, where the trocar is engaged with the second Luer connector.

7. The apparatus of claim 1, where the trocar is configured to be removed from the outer needle after the IO needle set has penetrated the bone.

8. An apparatus for penetrating a bone and associated bone marrow comprising:
   a housing;
   a drill shaft rotatably disposed within the housing;
   the drill shaft operable to connect the needle assembly to a reduction gear assembly disposed within the housing;
   a reduction gear assembly disposed in the housing and coupled to the drill shaft;
   a motor disposed within the housing and coupled to the reduction gear assembly;
   a battery power supply and associated circuitry disposed within the housing and configured to power the motor;
   an intraosseous (IO) needle assembly configured to penetrate the bone and associated bone marrow, the IO needle assembly comprising:
      an outer needle having a first end, a second end with a plurality of cutting surfaces, and a lumen extending from the first end to the second end;
      a first Luer connector disposed on the first end of the outer needle in fluid communication with the lumen;
      an inner trocar having a first end and a second end with a tip;
      where the inner trocar is disposed partially within the lumen and secured relative to the outer needle such that the tip of the inner trocar extends beyond the cutting surfaces of the outer needle;
   where the outer needle is configured to be coupled to the drive shaft via a second Luer connector to which the first Luer connector is connected.

9. The apparatus of claim 8, where the trocar is engaged with the second Luer connector.

10. The apparatus of claim 8, where the second Luer connector is releasably coupled to the drive shaft.

11. The apparatus of claim 10, where the trocar is engaged with the second Luer connector.

12. The apparatus of claim 8, where the first Luer connector is a male Luer connector.

13. The apparatus of claim 12, where the trocar is engaged with the second Luer connector.

14. The apparatus of claim 8, where the trocar is configured to be removed from the outer needle after the IO needle set has penetrated the bone.

* * * * *